(12) United States Patent
Holstein et al.

(10) Patent No.: US 12,083,137 B2
(45) Date of Patent: *Sep. 10, 2024

(54) TRIAZOLE BISPHOSPHONATE GERANYLGERANYL DIPHOSPHATE SYNTHASE INHIBITORS

(71) Applicants: BOARD OF REGENTS OF THE UNIVERSITY OF NEBRASKA, Lincoln, NE (US); UNIVERSITY OF IOWA RESEARCH FOUNDATION, Iowa City, IA (US)

(72) Inventors: Sarah Holstein, Omaha, NE (US); David Wiemer, Iowa City, IA (US)

(73) Assignees: BOARD OF REGENTS OF THE UNIVERSITY OF NEBRASKA, Lincoln, NE (US); UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 501 days.

This patent is subject to a terminal disclaimer.

(21) Appl. No.: 17/332,324

(22) Filed: May 27, 2021

(65) Prior Publication Data

US 2021/0393654 A1    Dec. 23, 2021

Related U.S. Application Data

(63) Continuation of application No. 16/605,564, filed as application No. PCT/US2018/029252 on Apr. 25, 2018, now Pat. No. 11,033,560.

(60) Provisional application No. 62/489,616, filed on Apr. 25, 2017.

(51) Int. Cl.
*A61K 31/683*    (2006.01)
*A61K 45/06*     (2006.01)
*C07F 9/6518*    (2006.01)

(52) U.S. Cl.
CPC ............ *A61K 31/683* (2013.01); *A61K 45/06* (2013.01); *C07F 9/6518* (2013.01)

(58) Field of Classification Search
CPC .................................. A61K 31/683; C07F 9/40
See application file for complete search history.

(56) References Cited

U.S. PATENT DOCUMENTS

2015/0005261 A1    1/2015   Hohl et al.

OTHER PUBLICATIONS

"Cancer Prevention Overview (PDQ®)—Patient Version", National Institutes of Health/National Cancer Institute, downloaded from the Internet at: <https://www.cancer.gov/about-cancer/causes-prevention/patient-prevention-overview-pdq> (2012).

"Targeted Cancer Therapies", National Institutes of Health/National Cancer Institute, downloaded from the Internet at: <https://www.cancer.gov/about-cancer/treatment/types/targeted-therapies/targeted-therapies-fact-sheet> (2015).

Agabiti et al., Molecular mechanisms linking geranylgeranyl diphosphate synthase to cell survival and proliferation, Mol. Membr. Biol., 33(1-2):1-11 (Mar. 2016).

Allen et al., Olefin Isomers of a Triazole Bisphosphonate Synergistically Inhibit Geranylgeranyl Diphosphate Synthase, Mol. Pharmacol., 91(3):229-36 (Mar. 2017).

Artyushin et al., Synthesis of camphecene derivatives using click chemistry methodology and study of their antiviral activity, Bioorg. Med. Chem. Lett., 27(10):2181-4 (May 2017).

Drake et al., Bisphosphonate therapeutics in bone disease: the hard and soft data on osteoclast inhibition, Mol. Interv., 10(3):141-52 (Jun. 2010).

Dykstra et al., Mechanisms for autophagy modulation by isoprenoid biosynthetic pathway inhibitors in multiple myeloma cells, Oncotarget, 6(39):41535-49 (Dec. 2015).

European Patent Application No. 18790712.6, Extended European Search Report, dated Jul. 22, 2020.

Foust et al., A new motif for inhibitors of geranylgeranyl diphosphate synthase, Bioorg. Med. Chem., 24(16):3734-41 (Aug. 2016).

Golub et al., Molecular classification of cancer: class discovery and class prediction by gene expression monitoring, Science, 286(5439):531-7 (1999).

Haney et al., Recent Advances in the Development of Mammalian Geranylgeranyl Diphosphate Synthase Inhibitors, Molecules, 22(6):E886 (May 2017).

Holstein et al., Isoprenoid biosynthetic pathway inhibition disrupts monoclonal protein secretion and induces the unfolded protein response pathway in multiple myeloma cells, Leuk. Res., 35(4):551-9 (Apr. 2011).

International Application No. PCT/US2018/029252, International Search Report and Written Opinion, mailed Aug. 1, 2018.

Matthiesen et al., alpha-Methylation enhances the potency of isoprenoid triazole bisphosphonates as geranylgeranyl diphosphate synthase inhibitors, 26(2):376-85 (Jan. 2018).

Matthiesen et al., Stereoselective Synthesis of Homoneryl and Homogeranyl Triazole Bisphosphonates, J. Org. Chem., 81(19):9438-42 (Oct. 2016).

(Continued)

*Primary Examiner* — Samantha L Shterengarts
*Assistant Examiner* — Karen Cheng
(74) *Attorney, Agent, or Firm* — MARSHALL, GERSTEIN & BORUN LLP

(57) ABSTRACT

Disclosed herein are inhibitors of the GGDPS enzyme, and methods for their use in treating or preventing diseases, such as multiple myeloma. The inhibitors described herein can include compounds of Formula (I) and pharmaceutically acceptable salts thereof:

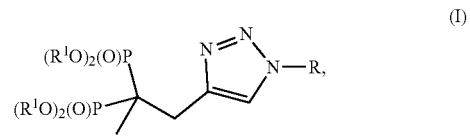

wherein the substituents are described.

20 Claims, 7 Drawing Sheets

(56) References Cited

OTHER PUBLICATIONS

McKenna et al., The facile dealkylation of phosphonic acid dialkyl esters by bromotrimethylsilane, Tetrahedron Lett., 2:155-158 (1977).

No et al., Lipophilic analogs of zoledronate and risedronate inhibit Plasmodium geranylgeranyl diphosphate synthase (GGPPS) and exhibit potent antimalarial activity, Proc. Natl. Acad. Sci. USA, 109(11):4058-63 (Mar. 2012).

Park et al., Human isoprenoid synthase enzymes as therapeutic targets, Front. Chem., 2:50 (Jul. 2014).

Reilly et al., Targeting geranylgeranylation reduces adrenal gland tumor burden in a murine model of prostate cancer metastasis, Clin. Exp. Metastasis, 32(6):555-66 (Aug. 2015).

Rodriguez et al., Approaches for Designing new Potent Inhibitors of Farnesyl Pyrophosphate Synthase, Expert. Opin. Drug Discov., 11(3):307-20 (2016).

Shiel et al., Amyloidosis, downloaded from the Internet at: <https://www.medicinenet.com/amyloidosis/article.htm> (2020).

Shull et al., Copper-mediated displacements of allylic THP ethers on a bisphosphonate template, J. Organometallic Chem., 690(10):2521-30 (May 2005).

Wills et al., Bishomoisoprenoid triazole bisphosphonates as inhibitors of geranylgeranyl diphosphate synthase, Bioorg. Med. Chem., 25(8):2437-44 (Apr. 2017).

Wills et al., Potent Triazole Bisphosphonate Inhibitor of Geranylgeranyl Diphosphate Synthase, ACS Med. Chem. Lett., 6(12):1195-8 (Oct. 2015).

Wills et al., Stereocontrolled regeneration of olefins from epoxides, Tetrahedron Lett., 57(12):1335-7 (2016).

Zhou et al., Geranyl and neryl triazole bisphosphonates as inhibitors of geranylgeranyl diphosphate synthase, Bioorg. Med. Chem., 22(9):2791-8 (May 2014).

Zhou et al., Triazole-based inhibitors of geranylgeranyltransferase II, Bioorg. Med. Chem. Lett., 23(3):764-6 (2013).

TRIAZOLE BISPHOSPHONATE GERANYLGERANYL DIPHOSPHATE SYNTHASE INHIBITORS

CROSS-REFERENCE TO RELATED APPLICATION

This is a continuation of U.S. patent application Ser. No. 16/605,564, filed Oct. 16, 2019, which is a 371 of PCT/US18/29252, filed Apr. 25, 2018, which claims benefit under 35 U.S.C. § 119(e) of U.S. Provisional Patent Application No. 62/489,616 filed Apr. 25, 2017, the disclosures thereof which are hereby incorporated by reference herein.

STATEMENT OF US GOVERNMENT SUPPORT

This invention is made with government support under Grant No. R01CA172070 awarded by the National Institutes of Health. The government has certain rights in the invention.

BACKGROUND

The mammalian isoprenoid biosynthetic pathway (IBP) is responsible for the synthesis of both steroidal and non-steroidal isoprenoids. The synthesis of the linear intermediates farnesyl diphosphate (FDP) and geranylgeranyl diphosphate (GGDP) is catalyzed by the enzymes FDP synthase (FDPS) and GGDP synthase (GGDPS), respectively. These two enzymes have been of interest from a therapeutic perspective, because both FDP and GGDP serve as isoprenoid donors for protein prenylation reactions. Several FDPS inhibitors have found clinical use in the treatment of bone disorders, including osteoporosis, myeloma bone disease, and metastatic bone disease. See Drake M T, Cremers S C. *Mol Interv.* 2010; 10:141-152. Due to their in vitro anti-cancer activity as well as antiparasitic activity, there is interest in the further development of FDPS inhibitors. See Rodriguez J B, Falcone B N, Szajnman S H. *Expert Opin Drug Discov.* 2016; 11:307-320; Park J, Matralis A N, Berghuis A M, Tsantrizos Y S. *Front Chem.* 2014; 2:50. While GGDPS inhibitors have not yet been examined in clinical trials, these agents also have potential as anti-cancer therapies among other diseases. See Agabiti S S, Liang Y, Wiemer A J. *Mol Membr Biol.* 2016; 1-11; Haney S L, Wills V S, Wiemer D F, Holstein S A. *Molecules.* 2017; 22:886. Inhibitors of GGDPS, by virtue of their ability to disrupt Rab GTPase geranylgeranylation, impair protein trafficking processes. This in turn can result in induction of the unfolded protein response pathway and ultimately apoptosis. See Holstein S A, Hohl R J. *Leuk Res.* 2011; 35:551-559; Dykstra K M, Allen C, Born E J, Tong H, Holstein S A. *Oncotarget.* 2015; 6:41535-41549.

Inhibition of protein from these cells results in programmed cell death, and represents a potential strategy for treatment of disease. Currently, the most potent inhibitor of GGDPS has been a mixture of isomers, which somewhat limits the clinical applicability as the precise composition of this mixture will vary amongst different preparations. There is a need for a more potent GGDPS inhibitor for use as a single isomer to limit the variability amongst composition mixtures.

SUMMARY

Provided herein are compounds that inhibit GGDPS and uses of inhibitors of GGDPS. In some cases, the compound disclosed herein has a structure of Formula (I), or a pharmaceutically acceptable salt thereof:

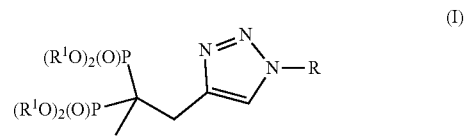

wherein: each $R^1$ comprises a protecting group, H, or M; R comprises $C_{10-15}$alkyl, $C_{10-15}$alkenyl, $C_{10-15}$hydroxyalkyl or $C_{10-15}$hydroxyalkenyl; and M is a metal ion selected from Li, Na, and K. In various cases, the compound is selected from the group consisting of

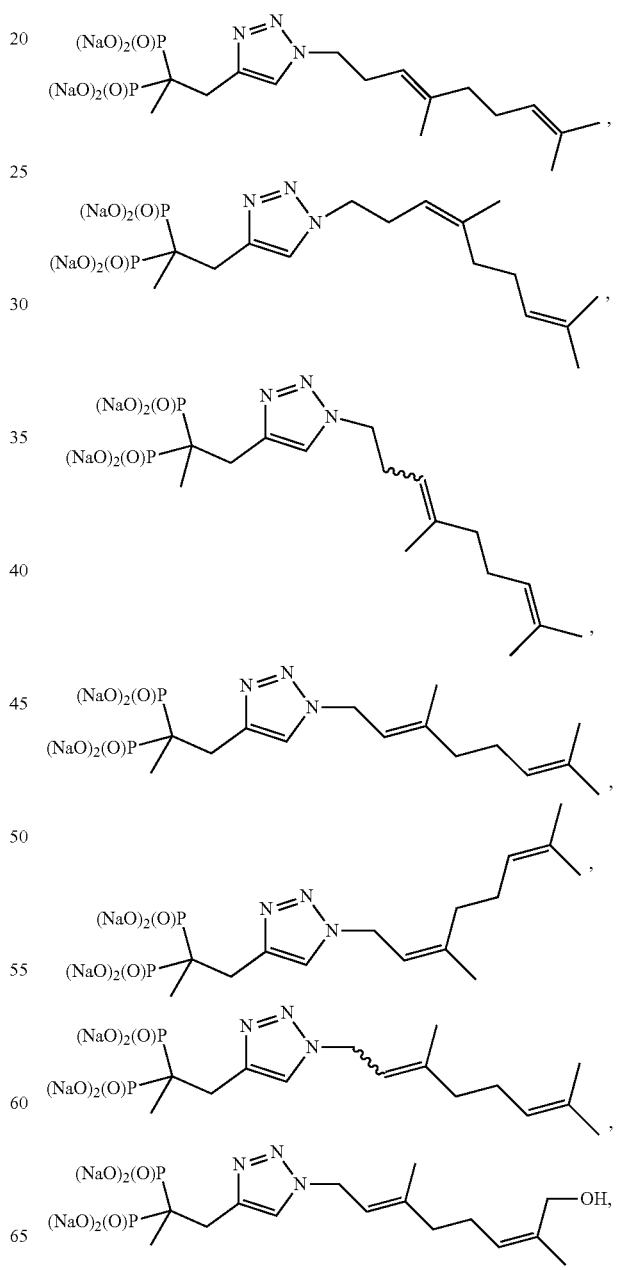

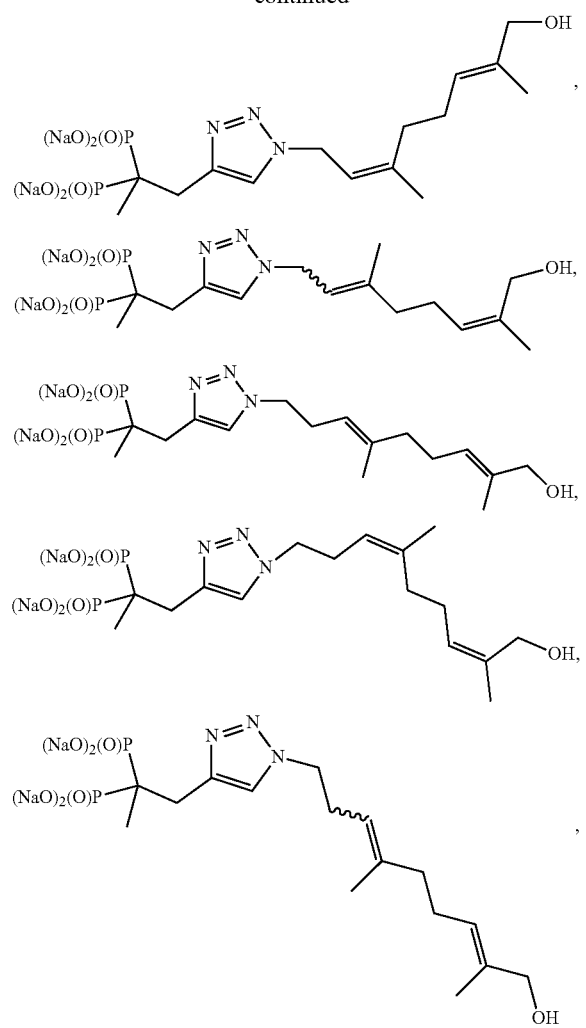

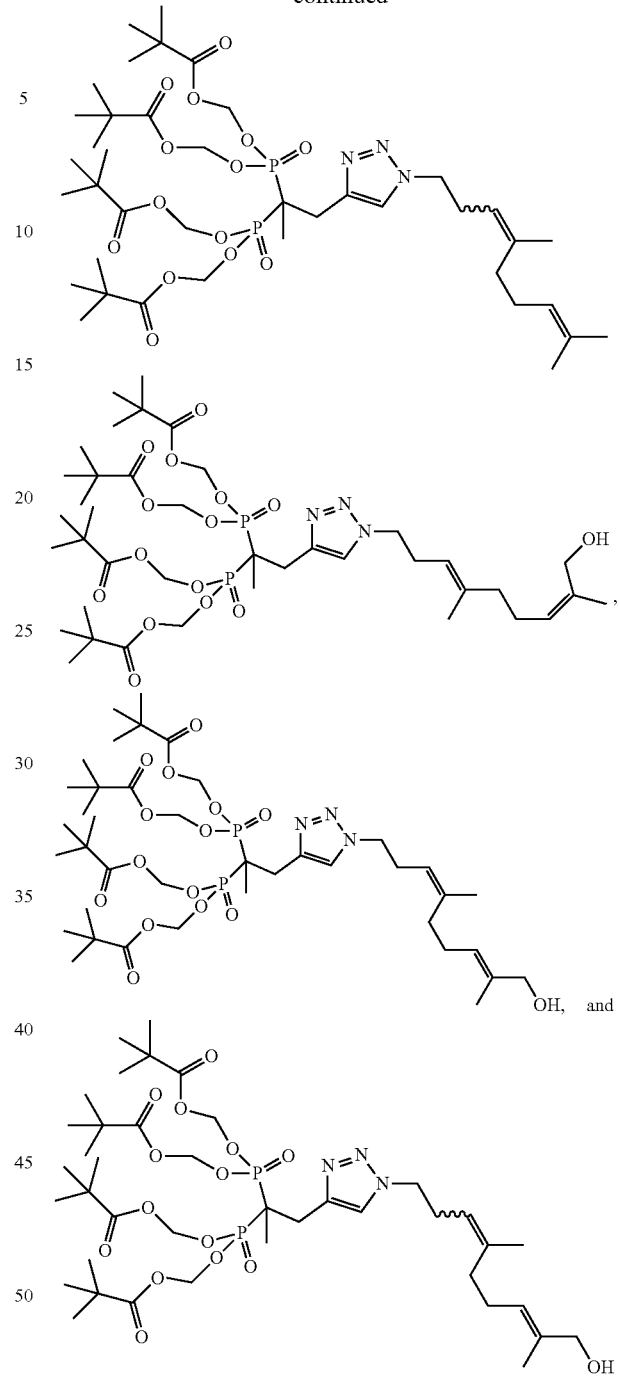

or a pharmaceutically acceptable salt thereof.

Also provided herein are methods of inhibiting GGDPS in a cell comprising contacting the cell with a compound or salt disclosed herein in an amount effective to inhibit GGDPS.

Further provided herein are methods of treating cancer in a subject comprising administering to the subject a therapeutically effective amount of a compound or salt as disclosed herein.

Also provided herein are methods of treating a disease associated with aberrant geranylgeranyl diphosphate synthase ("GGDPS") activity in a subject in need thereof,

DETAILED DESCRIPTION

Figure 1:
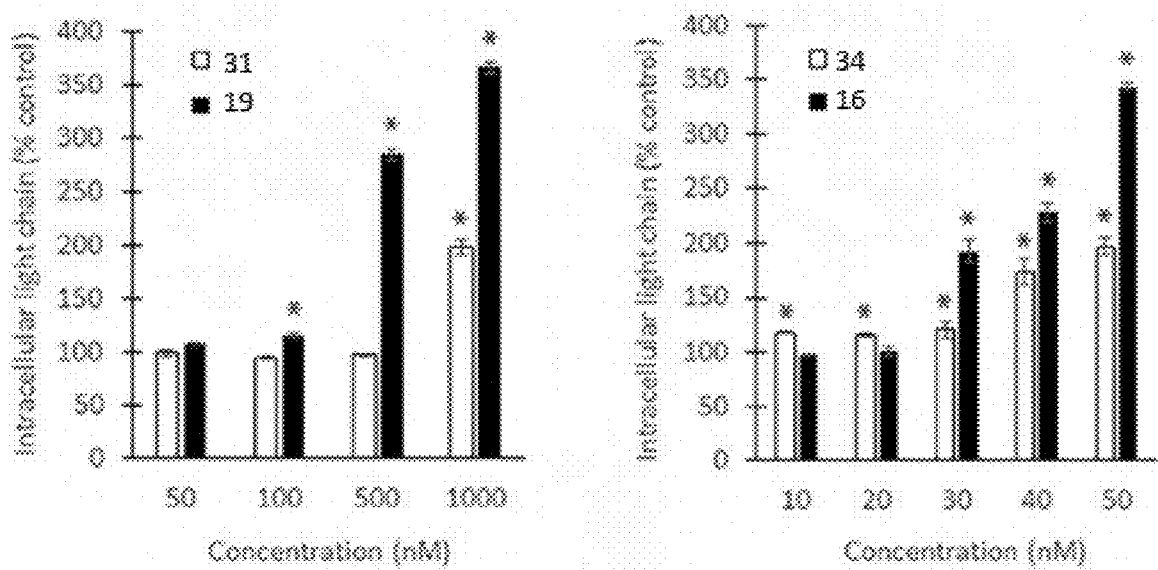
FIG. 1 shows the effects of the several α-methylated triazole bisphosphonate compounds as disclosed herein, compared to non-methylated compounds on protein geranylgeranylation. RPMI-8226 cells were incubated for 48 h in the presence or absence of lovastatin (Lov, 10 µM) or varying concentrations of the test compounds. Intracellular lambda light chain concentrations were determined via ELISA. Data are expressed as a percentage of control (mean±SD, n=3). The * denotes p<0.05 per unpaired two-tailed t-test.
Figure 2:
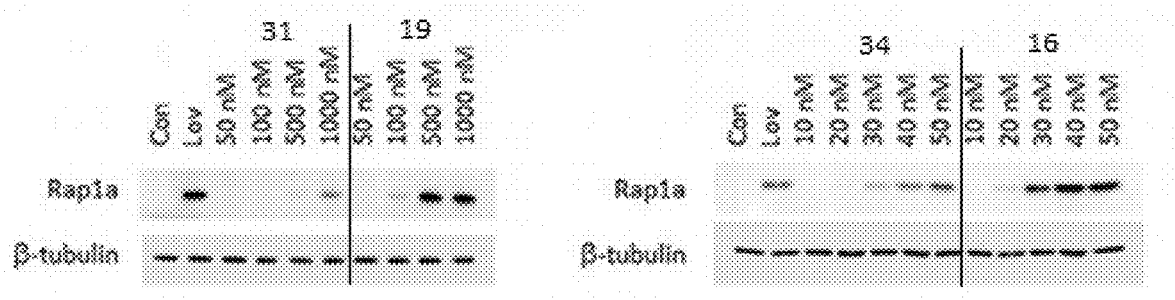
FIG. 2 shows the effects of several α-methylated triazole bisphosphonates, compared to non-methylated compounds on protein geranylgeranylation using immunoblot analysis of Rap1a (antibody detects only unmodified protein) and β-tubulin (as a loading control).

The present disclosure is directed to compounds which inhibit geranylgeranyl diphosphate synthase (GGDPS), and can be used in the treatment and prevention of diseases associated with GGDPS activity, such as cancer, amyloidosis, autoimmune disorders, and infectious disease. Specifically, the disclosure relates to triazole bisphosphonate based compounds, pharmaceutical compositions comprising said compounds and their methods of use thereof.

The compounds of the disclosure herein have several advantageous properties and effects. The compounds, for example: (1) can be purified and administered as single isomers, unlike the leading GGDPS inhibitor administered as a mixture of isomers limiting the clinical applicability, (2) can be synthesized as prodrugs of the triazole bisphosphonate compounds increasing activity in various embodiments, and (3) exhibit greater activity toward GGDPS inhibition than the leading GGDPS inhibitor.

Definitions

As used herein, "alkyl" refers to straight chained and branched saturated hydrocarbon groups containing one to thirty carbon atoms, for example, one to twenty carbon atoms, or one to ten carbon atoms, or ten to fifteen or ten to twenty carbon atoms. The term Cn means the alkyl group has "n" carbon atoms. For example, $C_4$ alkyl refers to an alkyl group that has 4 carbon atoms. $C_7$-$C_{20}$ alkyl refers to an alkyl group having a number of carbon atoms encompassing the entire range (i.e., 7 to 20 carbon atoms), as well as all subgroups (e.g., 7-19, 8-15, 7-17, 10-20, 7, 8, 9, 10, 11, 12, 13, 14, 15, 16, 17, 18, 19 and 20 carbon atoms). Unless otherwise indicated, an alkyl group can be an unsubstituted alkyl group or a substituted alkyl group. In some cases, the alkyl group is substituted with one or more hydroxy groups—a hydroxyalkyl. A hydroxyalkyl group comprises at least one OH group, and can comprise, e.g., 1, 2, 3, or 4 OH groups. With two or more OH groups, the OH groups are not on the same carbon, but on different carbons of the alkyl group.

As used herein, the term "alkenyl" is defined identically as "alkyl" except for containing at least one carbon-carbon double bond, and having two to thirty carbon atoms, for example, two to twenty carbon atoms, or two to ten carbon atoms, or ten to fifteen to ten to twenty carbon atoms. The term Cn means the alkenyl group has "n" carbon atoms. For example, $C_4$ alkenyl refers to an alkenyl group that has 4 carbon atoms. $C_7$-$C_{20}$ alkyl refers to an alkyl group having a number of carbon atoms encompassing the entire range (i.e., 7 to 20 carbon atoms), as well as all subgroups (e.g., 7-19, 8-15, 7-17, 10-20, 7, 8, 9, 10, 11, 12, 13, 14, 15, 16, 17, 18, 19 and 20 carbon atoms). Unless otherwise indicated, an alkenyl group can be an unsubstituted alkenyl group or a substituted alkenyl group. In some cases, the alkenyl group is substituted with one or more hydroxy groups—a hydroxyalkenyl. A hydroxyalkenyl group comprises at least one OH group, and can comprise, e.g., 1, 2, 3, or 4 OH groups. The OH group is not on the same carbon as a carbon of the double bond. With two or more OH groups, the OH groups are not on the same carbon, but on different carbons of the alkenyl group.

As used herein, the term "therapeutically effective amount" means an amount of a compound or combination of therapeutically active compounds (e.g., an inhibitor described herein, or a combination of inhibitors) that ameliorates, attenuates or eliminates one or more symptoms of a particular disease or condition (e.g., cancer), or prevents or delays the onset of one of more symptoms of a particular disease or condition.

As used herein, the terms "patient" and "subject" may be used interchangeably and mean animals, such as dogs, cats, cows, horses, and sheep (i.e., non-human animals) and humans. Particular patients are mammals (e.g., humans). The term patient includes males and females.

As used herein, the term "pharmaceutically acceptable" means that the referenced substance, such as a compound of the present disclosure, or a formulation containing the compound, or a particular excipient, are safe and suitable for administration to a subject or patient. The term "pharmaceutically acceptable carrier" refers to a medium that does not interfere with the effectiveness of the biological activity of the active ingredient(s) and is not toxic to the host to which it is administered.

As used herein the terms "treating", "treat" or "treatment" and the like include preventative (e.g., prophylactic) and palliative treatment.

As used herein, the term "excipient" means any pharmaceutically acceptable additive, carrier, diluent, adjuvant, or other ingredient, other than the active pharmaceutical ingredient (API).

The term "protecting group" as used herein refers to temporary substituents which protect a potentially reactive functional group from undesired chemical transformations. A phosphonic acid protecting group is a protecting group comprising the protection of a phosphonic acid functional group (e.g., trimethylsilyl, pivaloyloxymethyl, or an acetal). Conventional procedures for using such protecting groups as well as examples of suitable protecting groups are described, for example, in Greene et. al; *Protective Groups in Organic Synthesis,* 3rd ed.; John Wiley & Sons: New York, 1999; p. 178-179.

As used herein, the term "inhibitor" is meant to describe a compound that blocks or reduces activity of an enzyme or system of enzymes, receptors, or other pharmacological target. An inhibitor can act with competitive, uncompetitive, or noncompetitive inhibition. An inhibitor can bind reversibly or irreversibly, and therefore the term includes compounds that are suicide substrates of an enzyme. An inhibitor can modify one or more sites on or near the active site of the enzyme, or it can cause a conformational change elsewhere on the enzyme. The term inhibitor is used more broadly herein than scientific literature so as to also encompass other classes of pharmacologically or therapeutically useful agents, such as agonists, antagonists, stimulants, co-factors, and the like.

The use of the terms "a," "an," "the," and similar referents in the context of describing the invention (especially in the context of the claims) are to be construed to cover both the singular and the plural, unless otherwise indicated. Recitation of ranges of values herein merely is intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention. As used herein, the singular forms "a," "an," and "the" include plural referents unless the context clearly dictates otherwise.

As used herein, the terms "about" and "approximately" generally mean plus or minus 10% of the stated value. For example, about 0.5 would include 0.45 and 0.55, about 10 would include 9 to 11, about 1000 would include 900 to 1100.

Triazole Bisphosphonate Geranylgeranyl Diphosphate Synthase Inhibitors

Disclosed herein are compounds that can inhibit GGDPS enzymes. The compounds disclosed herein have a structure of Formula (I), or a pharmaceutically acceptable salt thereof:

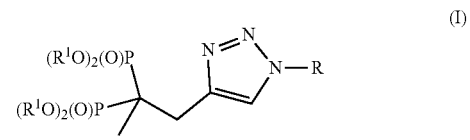

(I)

wherein:
  each $R^1$ comprises a protecting group, H, or M;
  R comprises $C_{10-15}$alkyl, $C_{10-15}$alkenyl, $C_{10-15}$hydroxyalkyl or $C_{10-15}$hydroxyalkenyl;
  M is a metal ion selected from Li, Na, and K.

In various cases, R is $C_{10-15}$alkyl, for example, $C_{10-12}$ (e.g., $C_{10}$alkyl, $C_{11}$alkyl, $C_{12}$alkyl) or $C_{13-15}$alkyl (e.g., $C_{13}$alkyl, $C_{14}$alkyl, $C_{15}$alkyl). In some embodiments, R is $C_{10-15}$alkenyl, for example, $C_{10-12}$alkenyl (e.g., $C_{10}$alkenyl, $C_{11}$alkenyl, $C_{12}$alkenyl), or $C_{13-15}$alkenyl (e.g., $C_{13}$alkenyl, $C_{14}$alkenyl, $C_{15}$alkenyl). In some cases, the $C_{10-15}$alkenyl comprises 1, 2, 3, 4 or 5 double bonds. In various embodiments, the $C_{10-15}$alkenyl comprises 1, 2, or 3 double bonds. In cases with two or more double bonds, the double bonds can be conjugated or isolated. In some cases, the double bonds are isolated. In some cases, the $C_{10-15}$ alkenyl comprises two double bonds. In select cases, the two double bonds are not conjugated (i.e., are isolated).

Also contemplated are compounds of Formula (I) wherein the alkyl or alkenyl is further substituted with at least one hydroxy group (i.e., a hydroxyalkyl or hydroxyalkenyl), e.g., one, two, three, or four hydroxy groups. In various cases, R is $C_{10-15}$hydroxyalkyl, for example, $C_{10-12}$ (e.g., $C_{10}$hydroxyalkyl, $C_{11}$hydroxyalkyl, $C_{12}$hydroxyalkyl) or $C_{13-15}$hydroxyalkyl (e.g., $C_{13}$hydroxyalkyl, $C_{14}$hydroxyalkyl, $C_{15}$hydroxyalkyl). In some embodiments, R is $C_{10-15}$hydroxyalkenyl, for example, $C_{10-12}$hydroxyalkenyl (e.g., $C_{10}$hydroxyalkenyl, $C_{11}$hydroxyalkenyl, $C_{12}$hydroxyalkenyl), or $C_{13-15}$-hydroxyalkenyl (e.g., $C_{13}$hydroxyalkenyl, $C_{14}$hydroxyalkenyl, $C_{15}$hydroxyalkenyl). In some cases, the $C_{10-15}$hydroxyalkenyl comprises 1, 2, 3, 4 or 5 double bonds. In various embodiments, the $C_{10-15}$hydroxyalkenyl comprises 1, 2, or 3 double bonds. In cases with two or more double bonds, the double bonds can be conjugated or isolated. In some cases, the double bonds are isolated. In some cases, the $C_{10-15}$ hydroxalkenyl comprises two double bonds. In select cases, the two double bonds are not conjugated (i.e., are isolated). A hydroxy substituent can be on any available carbon of the alkyl or alkenyl group. In some cases, the alkyl or alkenyl group is substituted with one or two OH groups.

Specifically contemplated R groups include those selected from the group consisting of:

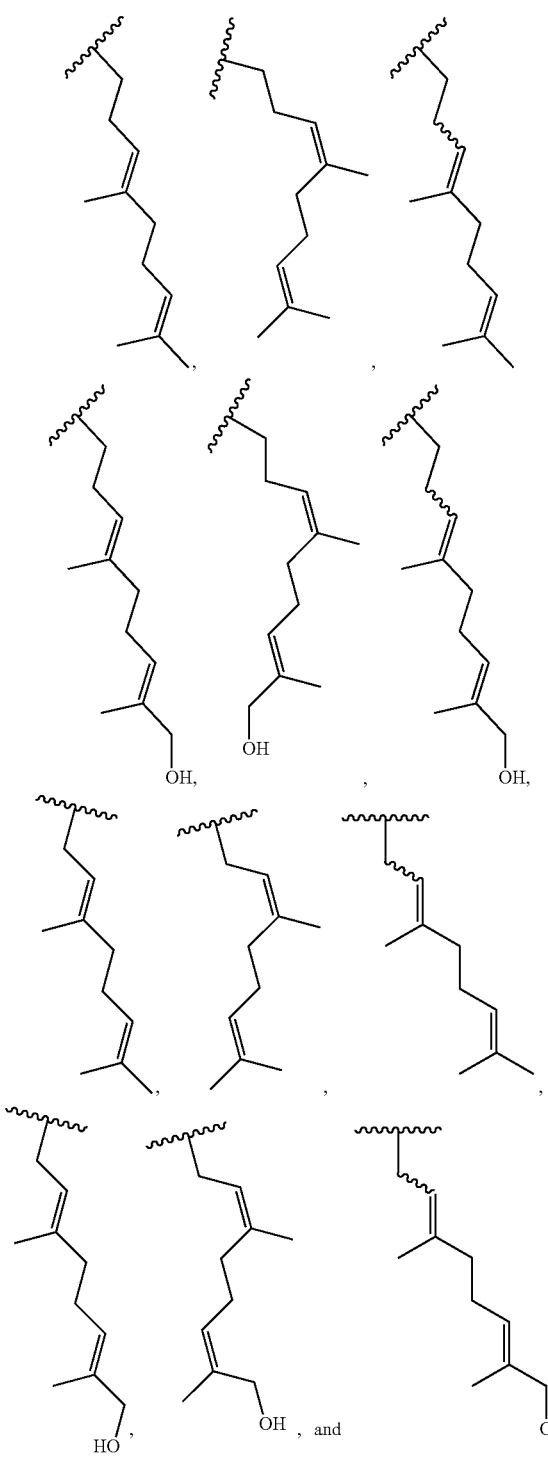

, , ,

, , ,

, , ,

OH, OH, OH,

, , ,

, , ,

HO, OH, and OH.

R[1] indicates the substituent on the (O)P—(OH)$_2$ moiety. In some cases the (O)P—(OH)$_2$ moiety is the phosphonic acid, i.e., R[1] is H. In some cases, the phosphonic acid is in salt form, e.g., R[1] is a metal ion, M. In some embodiments, M is an alkali metal, for example, R[1] can be Na, K or Li. In various embodiments, each R[1] is Na (e.g., the sodium salt).

In some embodiments, the phosphonic acid is in a protected form, e.g., R[1] is a protecting group of the OH functional groups of the (O)P—(OH)$_2$ moiety. Suitable protecting groups and the methods for protecting and deprotecting different substituents using such suitable protecting groups are well known to those skilled in the art; examples of which can be found in Greene et. al; *Protective Groups in Organic Synthesis,* 3rd ed.; John Wiley & Sons: New York, 1999; p. 178-179. Other suitable protecting groups are discussed in "Prodrugs of organophosphorus compounds: crossing the membrane barrier." Wiemer, A. J. and Wiemer, D. F. in *Topics in Current Chemistry,* V 360, *Phosphorus Chemistry* 1, Montchamp, J. L., Ed. 2015, 360, 115-160. In some cases, the protecting group is pivaloyloxymethyl ("POM"),

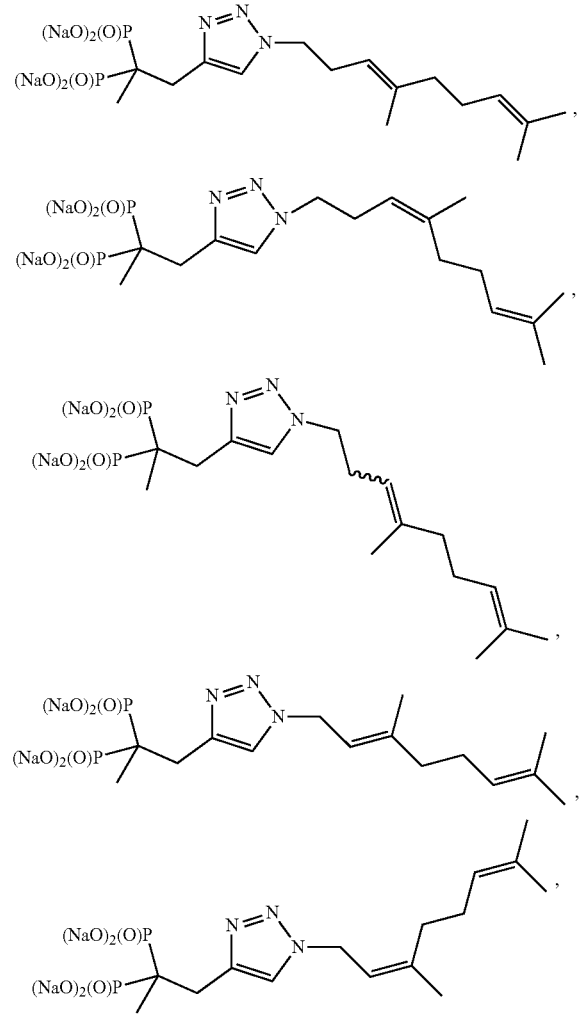

where the POM is attached to the oxygen of the OH group of the (O)P—(OH)$_2$ moiety.

Specific compounds of the disclosure include, but are not limited to, the following structures, or a pharmaceutically acceptable salt thereof:

-continued

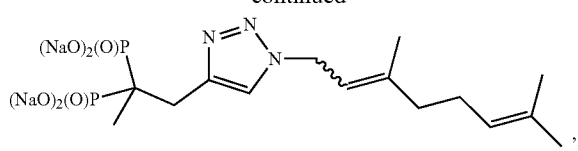
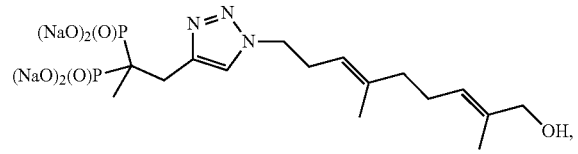
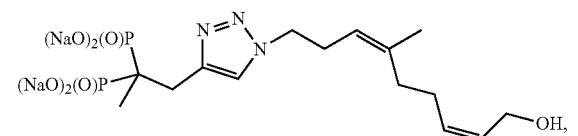
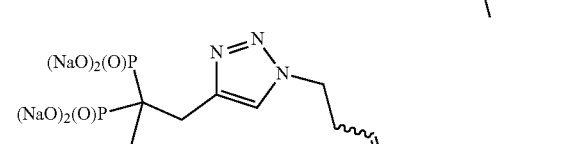
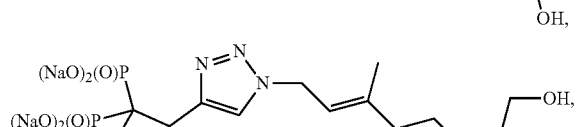
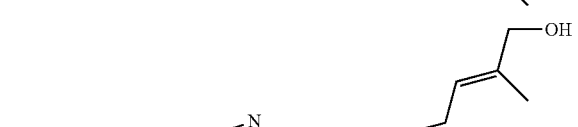
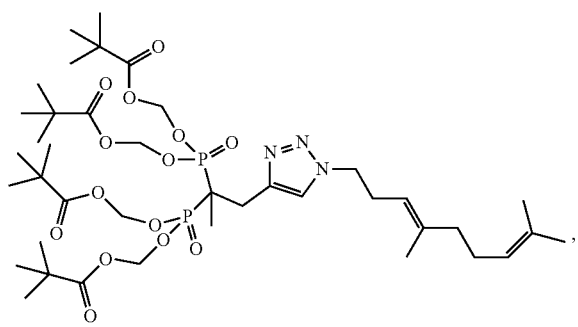

-continued

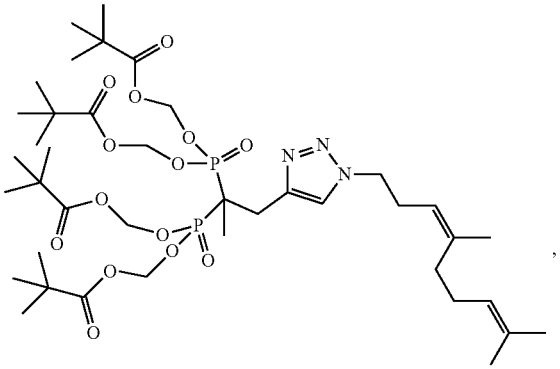
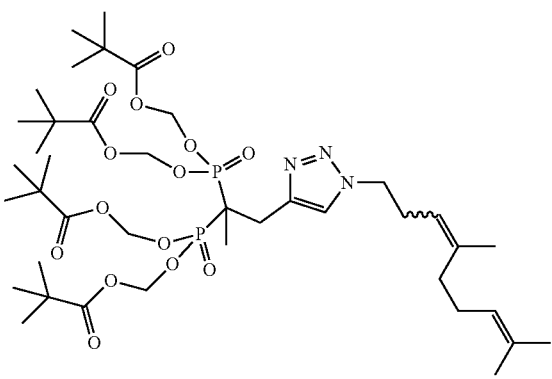
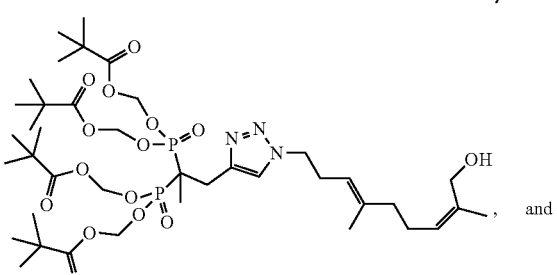
, and
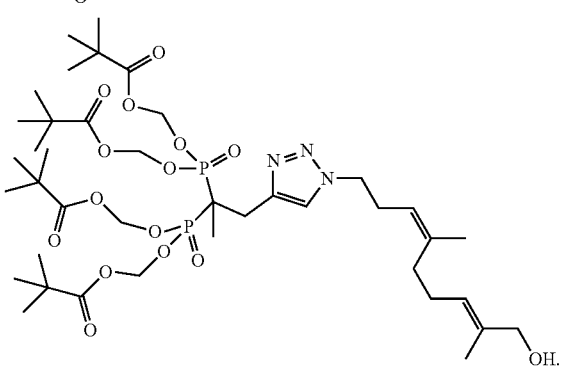

In various embodiments, the compounds disclosed herein can comprise more than one isomer. In some cases, the compounds disclosed herein can be synthesized as single isomers or as a mixture of two isomers. In some embodiments, the compounds herein can be synthesized as single isomers, for example, 17, 18, 20, or 21 (shown below). In various cases, the compounds herein can be a mixture of isomers, for example 16, 19, or 23 (shown below). In various embodiments, the compounds herein can be a mixture of isomers comprising an E and a Z isomer. In some cases, the compounds herein can be a mixture of isomers with a 1:10 to 1:1 E:Z ratio or a 10:1 to 1:1 E:Z ratio. In some cases, the compounds herein can be a mixture of isomers with a 1:5 to 1:1 E:Z ratio or a 5:1 to 1:1 E:Z ratio. In some embodiments, 16, 19, or 23 have about a 2:1 to 3:1 E:Z ratio.

Synthesis of Triazole Based Diphosphonates

The compounds herein can be synthesized by any method known to one skilled in the art. The schemes below depict methods for synthesizing the compounds of the disclosure (e.g., compounds of Formula (I)). For example, 1 or 2 can be reacted with 3 using "click" chemistry, [3+2] azide-alkyne cycloaddition, resulting in the triazole 4, 5, 6, 7, 8, or 9 (wherein 1 and 2 are either single E or Z isomers or a mixture of E and Z isomers).

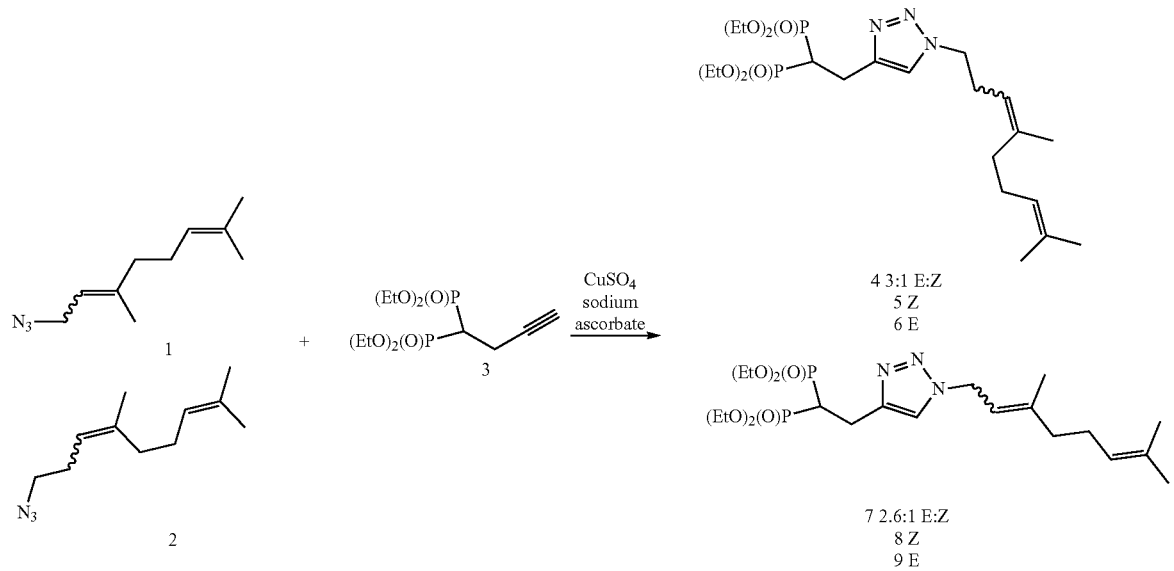

The triazole diphosphonates 4, 5, 6, 7, 8, or 9 can be α-methylated. For example, upon treatment with sodium hydride followed by methyl iodide, the E/Z-mixture, 7, as well as the individual Z and E isomers, 8 or 9 all undergo methylation smoothly. In a parallel fashion, the homologated compounds 10 (an E/Z mixture), 11 (the Z isomer), and 12 (the E isomer) were methylated in the same fashion.

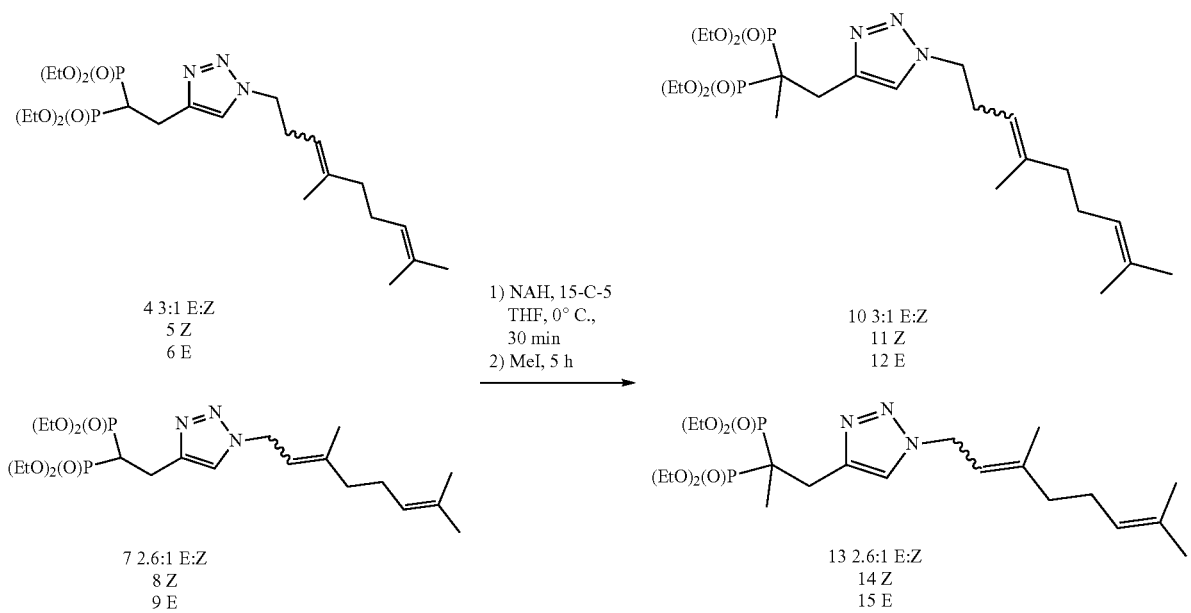

Compounds 10, 11, 12, 13, 14, or 15 can then be converted to the sodium salts. For example, 10, 11, 12, 13, 14, or 15 may be reacted using hydrolysis under the standard McKenna conditions to form the sodium salts 16, 17, 18, 19, 20, or 21 shown in the scheme below. All six of these new compounds were tested for biological activity, and the results (as explained in detail below) were sufficiently encouraging.

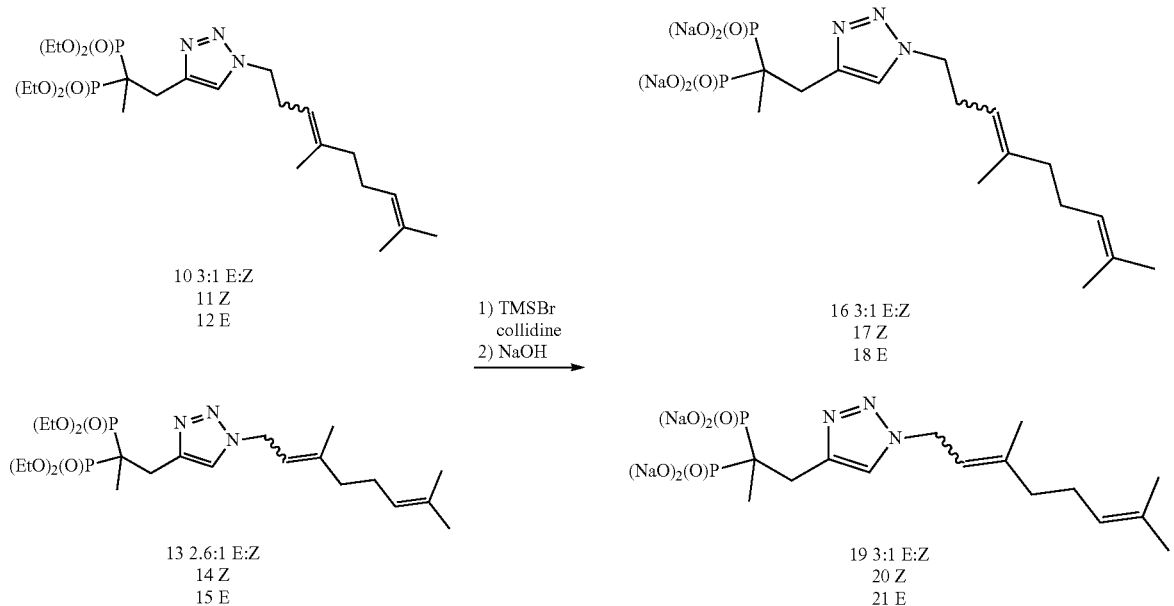

The triazole diphosphonates herein with the protecting group POM can be synthesized by any known method to those skilled in the art. For example, treatment of this tetramethyl ester with excess POMCl in the presence of sodium iodide gave the tetraPOM compound 22 in good yield. However, out of concern for the stability of this material, it was treated with the azide 2 after minimal purification to obtain the tetraPOM triazole 23, 24, or 25. This material then was employed in the cell-based bioassays described below.

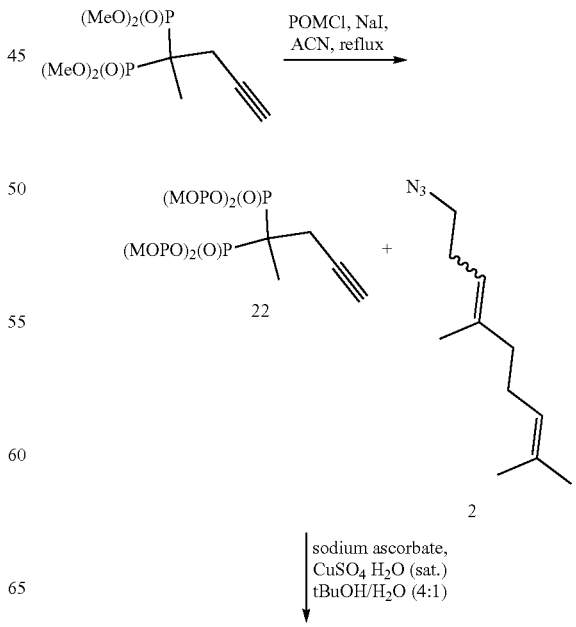

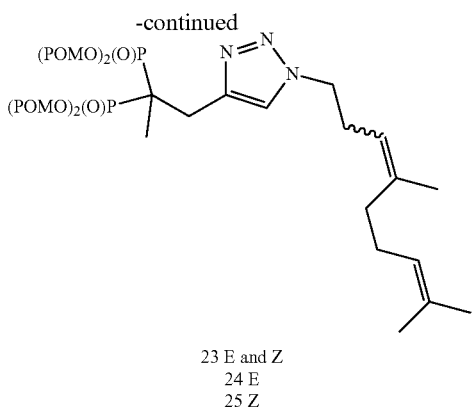

23 E and Z
24 E
25 Z

In addition to the α-methylated products, an α-ethylated analogue can be synthesized by any method known to those skilled in the art. For example, treatment of bisphosphonate 26 with sodium hydride and ethyl iodide gave the alkylated derivative 27 in modest yield, and hydrolysis of the ethyl esters proceeded under standard conditions to afford compound 28.

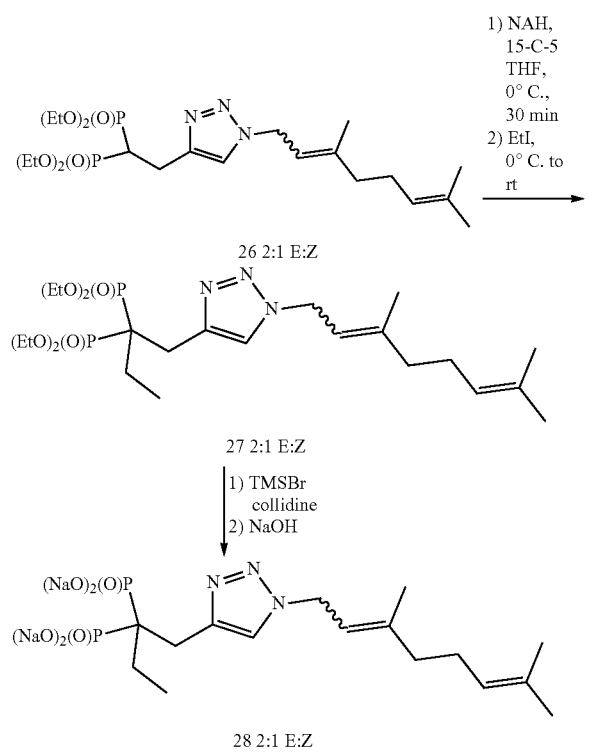

Additional synthetic procedures for preparing the compounds described herein can be found in the Examples section.

Pharmaceutical Formulations

Also provided herein are pharmaceutical formulations that include a compound as previously described herein (e.g., a compound of Formula (I), or a pharmaceutically acceptable salt thereof) and one or more pharmaceutically acceptable excipients.

The compounds described herein can be administered to a subject in a therapeutically effective amount. The compounds can be administered alone or as part of a pharmaceutically acceptable composition or formulation. In addition, the compounds can be administered all at once, multiple times, or delivered substantially uniformly over a period of time. It is also noted that the dose of the compound can be varied over time.

The compounds disclosed herein and other pharmaceutically active compounds, if desired, can be administered to a patient or subject by any suitable route, e.g. orally, rectally, parenterally, (for example, intravenously, intramuscularly, or subcutaneously) intracisternally, intravaginally, intraperitoneally, intravesically, or as a buccal, inhalation, or nasal spray. The administration can be to provide a systemic effect (e.g. eneteral or parenteral). All methods that can be used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. The solid dosage forms may also contain opacifying agents.

Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferably suppositories, which can be prepared by mixing the compounds of the disclosure with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

The compounds described herein can be administered to a patient or subject at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that will be used can potentially depend on a number of factors, including the requirements of the patient or subject, the severity of the condition or disease being treated, and the pharmacological activity of the compound being administered. The determination of dosage ranges and optimal dosages for a particular patient or subject is within the ordinary skill in the art.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

Methods of Use

The compounds described herein (e.g., the compounds of Formula (I) and pharmaceutically acceptable salts thereof) can inhibit GGDPS. Some diseases are characterized by the over activity of GGDPS and cells that are over active in respect to protein synthesis and export. As such, further provided are methods of treating or preventing disease (e.g., cancer) using the compounds described herein. In some cases, the compounds described herein (e.g., the compounds of Formula (I) and pharmaceutically acceptable salts thereof) inhibit GGDPS with an $IC_{50}$ of about 25 µM or less. In some embodiments, the compounds described herein (e.g., the compounds of Formula (I) and pharmaceutically acceptable salts thereof) have an $IC_{50}$ value for GGDPS of less than about 5 µM, or less than about 3 µM, or less than about 2 µM, or less than about 1 µM, or less than about 0.9 µM, or less than about 0.8 µM, or less than about 0.7 µM, or less than about 0.6 µM, or less than about 0.5 µM, or less than about 0.2 µM or less than about 0.1 µM. In various cases, the $IC_{50}$ value of the compounds described herein (e.g., the compounds of Formula (I), and pharmaceutically acceptable salts thereof) is about 0.001 µM to about 1 µM, or about 0.01 µM to about 1 µM.

Thus, provided herein are methods of inhibiting GGDPS in a cell comprising contacting the cell with a compound described herein (e.g., a compound of Formula (I) or a pharmaceutical salt thereof), in an amount effective to inhibit the GGDPS. The contacting of the cell can occur in vitro or in vivo. The compound described herein can contact a cell in vivo by administering a compound described herein to a subject in need of GGDPS inhibition. Therefore, the disclosure includes administering one or more of a compound described herein to a subject, such as a human, in need thereof. In some embodiments, the subject suffers from cancer, amyloidosis, autoimmune disorders and infectious disease.

In view of the above, in various embodiments, the disclosure includes a method of treating a disease in a subject. The compositions herein can be used to treat a variety of diseases to a subject in need of GGDPS inhibition. In various embodiments, the compounds disclosed herein can be used to treat a disease associated with GGDPS activity, such as cancer, amyloidosis, an autoimmune disorder, or an infectious disease. In some cases, the compounds disclosed herein can be used to treat cancer in a subject. In some embodiments, cancer is selected from a group consisting of leukemia, lymphoma, bone cancer, prostate cancer, breast cancer, sarcoma, lung cancer, bladder cancer, multiple myeloma, skin cancer, brain cancer, thyroid cancer, stomach cancer, ovarian cancer, liver cancer, and colon cancer. In various embodiments, the cancer is multiple myeloma.

Combination Therapy

The compounds herein can be administered with one or more additional pharmaceutically active compounds/agents. In some embodiments, the compounds described herein can be administered to the subject with a second therapeutic. In various cases, the second therapeutic is an anti-cancer agent. Contemplated anti-cancer agents include aspirin, sulindac, curcumin, alkylating agents, nitrogen mustard, mechlorethamine, cyclophosphamide, ifosfamide, melphalan, chlorambucil, nitrosourea, carmustine (BCNU), lomustine (CCNU), semustine (methyl-CCNU); ethylenimine, methylmelamine, thriethylenemelamine (TEM), triethylene, thiophosphoramide (thiotepa), hexamethylmelamine (HMM, altretamine); alkyl sulfonate, busulfan; triazine, dacarbazine (DTIC); a folic acid analog, methotrexate, trimetrexate, pyrimidine analog, 5-fluorouracil, fluorodeoxyuridine, gemcitabine, cytosine arabinoside (AraC, cytarabine), 5-azacytidine, 2,2'-difluorodeoxycytidine, purine analog, 6-mercaptopurine, 6-thioguanine, azathioprine, 2'-deoxycoformycin (pentostatin), erythrohydroxynonyladenine (EHNA), fludarabine phosphate, 2-chlorodeoxyadenosine (cladribine, 2-CdA); antimitotic drug, paclitaxel, *vinca* alkaloid, vinblastine (VLB), vincristine, vinorelbine, taxotere, estramustine, estramustine phosphate; epipodophylotoxin, etoposide, teniposide; antibiotic, actimomycin D, daunomycin (rubidomycin), doxorubicin, mitoxantrone, idarubicin, bleomycins, plicamycin (mithramycin), mitomycinC, actinomycin; L-asparaginase; interferon-alpha, IL-2, G-CSF, GM-CSF; platinum coordination complex, cisplatin, carboplatin, anthracenedione, mitoxantrone, hydroxyurea, methylhydrazine derivative, N-methylhydrazine (MIH), procarbazine, adrenocortical suppressant, mitotane (o,p'-DDD), aminoglutethimide; adrenocorticosteroid antagonist, prednisone, dexamethasone, aminoglutethimide; progestin, hydroxyprogesterone caproate, medroxyprogesterone acetate, megestrol acetate; estrogen, diethylstilbestrol, ethinyl estradiol; antiestrogen, tamoxifen; androgen, testosterone propionate, fluoxymesterone; antiandrogen, flutamide, gonadotropin-releasing hormone analog, leuprolide; nonsteroidal antiandrogen, flutamide; kinase inhibitor, histone deacetylase inhibitor, methylation inhibitor, proteasome inhibitor, monoclonal antibody, oxidant, anti-oxidant, telomerase inhibitor, $BH_3$ mimetic, ubiquitin ligase inhibitor, immunomodulatory drug, checkpoint inhibitor, and a stat inhibitor.

When a patient or subject is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions might be different forms. For example, one or more compound may be delivered via a tablet, while another is administered via injection or orally as a syrup. All combinations, delivery methods and administration sequences are contemplated.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment.

Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

EXAMPLES

Materials and Methods

Tetrahydrofuran was freshly distilled from sodium/benzophenone, while methylene chloride was distilled from calcium hydride prior to use. All other reagents and solvents were purchased from commercial sources and used without further purification. All reactions in nonaqueous solvents were conducted in flame-dried glassware under a positive pressure of argon and with magnetic stirring. All NMR spectra were obtained at 300 MHz for $^1$H, and 75 MHz for $^{13}$C, with internal standards of $(CH_3)_4Si$ ($^1$H, 0.00) or $CHCl_3$ (1H, 7.27; $^{13}$C, 77.2 ppm) for non-aqueous samples or $H_2O$ ($^1$H, 4.80) and 1,4-dioxane ($^{13}$C, 66.7 ppm) for aqueous samples. The $^{31}$P chemical shifts were reported in ppm relative to 85% $H_3PO_4$ (external standard). High resolution mass spectra were obtained at the University of Iowa Mass Spectrometry Facility. Silica gel (60 Å, 0.040-0.063 mm) was used for flash chromatography.

Example 1: Sodium (1-(1-(3,7-dimethylocta-2,6-dien-1-yl)-1H-1,2,3-triazol-4-yl)propane-2,2-diyl)bis(phosphonate) (19)

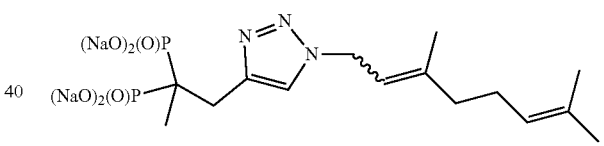

Under standard conditions (see Zhou et al. *Bioorg Med Chem*. 2014; 22:2791-2798; McKenna et al.; *Tetrahedron Lett*. 1977; 18:155-158) to a stirred solution of the ethyl ester 13 (523 mg, 1.01 mmol) in $CH_2Cl_2$ (17 mL) at 0° C., collidine (9.4 mL, 7.07 mmol) and TMSBr (97%, 1.1 mL, 8.45 mmol) were added dropwise in succession. The reaction was allowed to stir overnight while it warmed to room temperature, and the solvent then was removed in vacuo. The resulting residue was diluted with toluene (30 mL) and concentrated in vacuo to remove any excess TMSBr (3×). The residue was treated with 2N NaOH (3.4 mL, 6.8 mmol) and the solution was allowed to stir overnight at room temperature. Anhydrous acetone was added and the mixture was placed in the freezer for 20 min. The resulting solid was collected by filtration and dissolved in water, and the solution was diluted with anhydrous acetone. This mixture was placed in the freezer for 20 min. The resulting solid was collected by filtration, dissolved in water, and lyophilized to provide the desired salt 19 (333 mg, 67%) as a white powder. Reported below is the data for the mixture of E and Z isomers for the $^1$H NMR spectrum and the major isomer in the $^{13}$C NMR spectrum: $^1$H NMR (300 MHz, $D_2O$) δ 7.90 (s, 1H), 5.54-5.40 (m, 1H), 5.17-5.09 (m, 1H), 4.92 (t, J=6.8 Hz, 2H), 3.16 (t, $J_{HP}$=13.1 Hz, 2H), 2.26-2.05 (m, 4H), 1.76

(s, 3H), 1.62 (s, 3H), 1.57-1.55 (m, 3H), 1.06 (t, $J_{HP}$=14.5 Hz, 3H); $^{13}$C NMR (75 MHz, D$_2$O) δ 146.8 (t, $J_{CP}$=8.9 Hz), 143.2, 133.8, 125.8, 124.0, 117.5, 47.9, 41.0 (t, $J_{CP}$=120.1 Hz), 38.7, 30.1, 25.6, 25.0, 18.8 (t, $J_{CP}$=4.0 Hz), 17.1, 15.8; $^{31}$P NMR (121 MHz, D$_2$O) δ 23.9; HRMS (ES$^-$) m/z calcd for C$_{15}$H$_{22}$N$_3$O$_6$P$_2$ (M–H)$^-$ 406.1297, found 406.1302.

Example 2: Sodium (Z)-(1-(1-(3,7-dimethylocta-2,6-dien-1-yl)-1H-1,2,3-triazol-4-yl)propane-2,2-diyl)bis(phosphonate) (20)

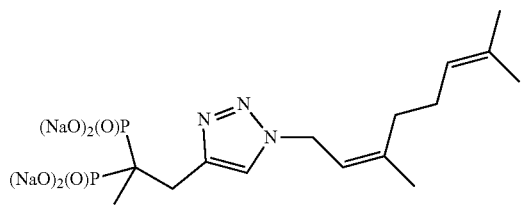

As described above for compound 19, the ethyl ester 14 (200 mg, 0.38 mmol) in CH$_2$Cl$_2$ (6.4 mL) at 0° C. was treated with, collidine (0.35 mL, 2.66 mmol) and TMSBr (97%, 0.42 mL, 1.62 mmol). A parallel workup provided the desired salt 20 (55 mg, 29%) as a white powder: $^1$H NMR (300 MHz, D$_2$O) δ 7.78 (s, 1H), 5.44-5.37 (m, 1H), 5.05-4.97 (m, 1H), 4.81 (t, J=7.3 Hz, 2H), 3.09-3.00 (m, 2H), 2.15-1.98 (m, 4H), 1.66 (d, J=0.8 Hz, 3H), 1.52 (s, 3H), 1.47 (s, 3H), 0.96 (t, $J_{HP}$=15.0 Hz, 3H); $^{13}$C NMR (75 MHz, D$_2$O) δ 146.7 (t, $J_{CP}$=9.0 Hz), 143.6, 134.0, 125.6, 123.7, 117.9, 47.7, 41.0 (t, $J_{CP}$=119.5 Hz), 31.4, 30.0, 25.8, 25.0, 22.6 18.7 (t, $J_{CP}$=4.0 Hz), 17.1; $^{31}$P NMR (121 MHz, D$_2$O) δ 23.9; HRMS (ES$^-$) m/z calcd for C$_{15}$H$_{23}$N$_3$O$_6$P$_2$ (M–H)$^-$ 406.1297, found 406.1304.

Example 3: Sodium (E)-(1-(1-(3,7-dimethylocta-2,6-dien-1-yl)-1H-1,2,3-triazol-4-yl)propane-2,2-diyl)bis(phosphonate) (21)

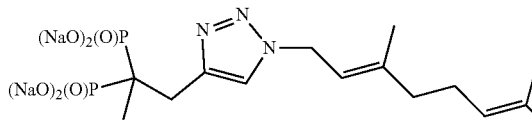

As described above for compound 19, the ethyl ester 15 (100 mg, 0.19 mmol) in CH$_2$Cl$_2$ (3.2 mL) at 0° C. was treated with collidine (0.18 mL, 1.33 mmol) and TMSBr (97%, 0.21 mL, 1.62 mmol). A parallel workup provided the desired salt 21 (41 mg, 43%) as a white powder: $^1$H NMR (300 MHz, D$_2$O) δ 7.72 (s, 1H), 5.37-5.31 (m, 1H), 5.04-4.95 (m, 1H), 4.85 (d, J=7.3 Hz, 2H), 3.13-3.04 (m, 2H), 2.05-1.96 (m, 4H), 1.66 (s, 3H), 1.52 (s, 3H), 1.44 (m, 3H), 1.16 (t, $J_{HP}$=15.4 Hz, 3H); $^{13}$C NMR (75 MHz, D$_2$O) δ 144.1 (m), 143.7, 133.8, 125.3, 124.0, 117.2, 47.9, 40.3 (t, $J_{CP}$=116.3 Hz), 38.6, 28.0, 25.5, 24.9, 17.0, 16.8 (t, $J_{CP}$=4.1 Hz), 15.7; $^{31}$P NMR (121 MHz, D$_2$O) δ 23.5; HRMS (ES$^-$) m/z calcd for C$_{15}$H$_{23}$N$_3$O$_6$P$_2$(M–H)$^-$ 406.1297, found 406.1295.

Example 4: Sodium (E)-(1-(1-(4,8-dimethylnona-3,7-dien-1-yl)-1H-1,2,3-triazol-4-yl)propane-2,2-diyl)bis(phosphonate) (18)

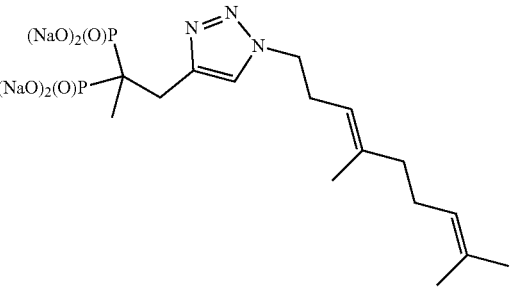

As described above for compound 19, the bisphosphonate ester 12 (390 mg, 0.73 mmol) in CH$_2$Cl$_2$ (12 mL) at 0° C. was treated with collidine (0.68 mL, 5.12 mmol) and TMSBr (97%, 0.79 mL, 6.14 mmol). Standard workup provided the desired salt compound 18 (290 mg, 78%) as a white powder: $^1$H NMR (300 MHz, D$_2$O) δ 7.78 (s, 1H), 5.09-4.94 (m, 2H), 4.24 (t, J=6.9 Hz, 2H), 3.16 (t, $J_{HP}$=13.3 Hz, 2H), 2.57 (dt, J=6.8 Hz, J=6.8 Hz, 2H), 1.98-1.88 (m, 4H), 1.65 (s, 6H), 1.58 (s, 3H), 1.08 (t, $J_{HP}$=15.0 Hz, 3H); $^{13}$C NMR (75 MHz, D$_2$O) δ 146.3 (t, $J_{CP}$=9.0 Hz), 140.0, 133.6, 126.0, 124.3, 119.3, 50.0, 40.7 (t, $J_{CP}$=117.3 Hz), 38.9, 29.6 (m), 28.4, 25.8, 25.0, 18.7 (t, $J_{CP}$=3.8 Hz), 17.1, 15.2; $^{31}$P (121 MHz, D$_2$O) 23.7 ppm; HRMS (ES$^-$) m/z calcd for C$_{16}$H$_{28}$N$_3$O$_6$P$_2$ (M–H)$^-$ 420.1453, found 420.1454

Example 5: Sodium (Z)-(1-(1-(4,8-dimethylnona-3,7-dien-1-yl)-1H-1,2,3-triazol-4-yl)propane-2,2-diyl)bis(phosphonate) (17)

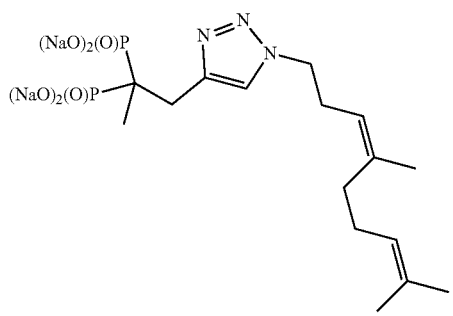

As described above for compound 19, the bisphosphonate ester 11 (551 mg, 1.03 mmol) in CH$_2$Cl$_2$ (17 mL) at 0° C. was treated with collidine (0.95 mL, 7.22 mmol) and TMSBr (97%, 1.15 mL, 8.67 mmol). Standard workup provided the desired salt 17 (293 mg, 56%) as a white powder: $^1$H NMR (300 MHz, D$_2$O) δ 7.89 (s, 1H), 5.18-5.08 (m, 2H), 4.33 (t, J=6.7 Hz, 2H), 3.16 (t, $J_{HP}$=13.3 Hz, 2H), 2.57 (dt, J=6.8 Hz, J=6.8 Hz, 2H), 1.98-1.88 (m, 4H), 1.65 (s, 6H), 1.58 (s, 3H), 1.08 (t, $J_{HP}$=15.0 Hz, 3H); $^{13}$C NMR (75 MHz, D$_2$O) δ 146.8 (t, $J_{CP}$=9.1 Hz), 140.6, 134.3, 126.7, 124.7, 120.6, 50.7, 41.3 (t, $J_{CP}$=118.2), 31.5, 30.1, 28.9, 26.3, 25.5, 23.1, 19.2 (t, $J_{CP}$=3.8 Hz), 17.6; $^{31}$P (121 MHz, D$_2$O) 23.8; HRMS (ES$^-$) m/z calcd for C$_{16}$H$_{28}$N$_3$O$_6$P2 (M–H)$^-$ 420.1453, found 420.1454.

Example 6: Sodium (1-(1-(4,8-dimethylnona-3,7-dien-1-yl)-1H-1,2,3-triazol-4-yl)propane-2,2-diyl)bis(phosphonate) (16)

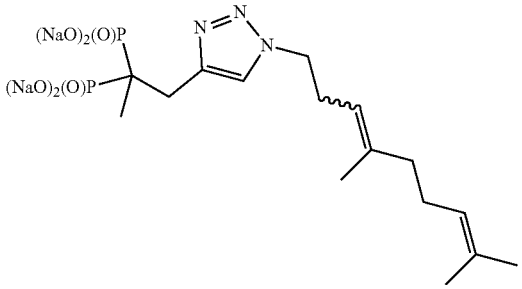

As described above for compound 19, the ethyl ester 10 (144 mg, 0.27 mmol) in CH$_2$Cl$_2$ (4.5 mL) at 0° C. was treated with collidine (0.25 mL, 1.89 mmol) and TMSBr (97%, 0.30 mL, 2.27 mmol). Standard workup provided the desired salt 16 (48 mg, 35%) as a white powder. Reported is the mixture of E and Z isomers for the 1H NMR spectrum and the major isomer in the $^{13}$C NMR spectrum: $^1$H NMR (300 MHz, D$_2$O) δ 7.91 (s, 1H), 5.19-5.07 (m, 2H), 4.40-4.33 (m, 2H), 3.18 (t, J$_{HP}$=13.2 Hz, 2H), 2.59 (dt, J=7.0 Hz, J=7.0 Hz, 2H), 2.09-1.90 (m, 4H), 1.67 (s, 3H), 1.59 (s, 3H), 1.44 (3H), 1.15 (t, J$_{HP}$=14.9 Hz, 3H); $^{13}$C NMR (75 MHz, D$_2$O) δ 145.6 (t, J$_{CP}$=9.3 Hz), 140.1, 133.7, 125.8, 124.4, 119.3, 50.1, 40.4 (t, J$_{CP}$=115.0 Hz), 38.9, 28.7, 28.3, 25.8, 25.0, 18.6 (t, J$_{CP}$=3.9 Hz), 17.1, 15.1; $^{31}$P (121 MHz, D$_2$O) 23.3 ppm; HRMS (ES$^-$) m/z calcd for C$_{18}$H$_{28}$N$_3$O$_6$P$_2$ (M–H)$^-$ 420.1453, found 420.1451.

Example 7: (Z)-(((1-(1-(4,8-dimethylnona-3,7-dien-1-yl)-1H-1,2,3-triazol-4-yl)propane-2,2-diyl)bis(oxo-15-phosphanetriyl))tetrakis(oxy))tetrakis(methylene) tetrakis(2,2-dimethylpropanoate) (25)

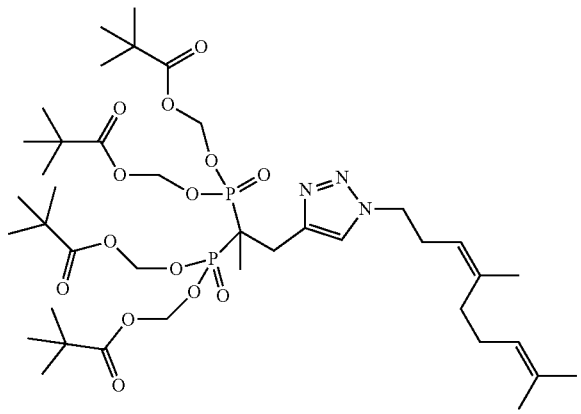 [SMILES: CC(C)=CCC/C(C)=C\CCn1cc(CC(C)(P(=O)(OCOC(=O)C(C)(C)C)OCOC(=O)C(C)(C)C)P(=O)(OCOC(=O)C(C)(C)C)OCOC(=O)C(C)(C)C)nn1]

To a stirred solution of compound 22 (764 mg, 1.12 mmol) and homoneryl azide (324 mg, 1.67 mmol) in t-BuOH/H$_2$O (4:1, 11 mL total), saturated CuSO$_4$ (0.01 mL) and sodium ascorbate (67 mg, 0.34 mmol) were added in sequence. The resulting reaction mixture was allowed to stir for five days at room temperature, and the solvent then was removed in vacuo. The resulting residue was dissolved in brine and extracted with EtOAc (5×). The combined organic extracts were washed with 5% NH$_4$OH, dried (Na$_2$SO$_4$) and filtered, and the filtrate was concentrated in vacuo to afford the crude triazole 25 (707 mg, 72%) as a yellow oil. Further purification of a portion (55 mg) via HPLC on a C-8 5 μM 250×10 mm Restek column scanning at a wave length of 210 nm afforded pure compound 25 (24 mg, 44%) as a light yellow oil material that was used in the bioassays: $^1$H NMR (300 MHz, CDCl$_3$) δ 7.51 (s, 1H), 5.74-5.64 (m, 8H), 5.14-5.04 (m, 2H), 4.32-4.24 (m, 2H), 3.30 (dd, J$_{HP}$=16.0 Hz, J$_{HP}$=16.0 Hz, 2H), 2.58 (dt, J=7.4 Hz, J=7.3 Hz, 2H), 2.04-1.97 (m, 4H), 1.69 (d, J=1.1 Hz, 3H), 1.67 (s, 3H), 1.59 (s, 3H), 1.48 (t, J=17.7 Hz, 3H), 1.23-1.22 (m, 36H); $^{13}$C NMR (75 MHz, CDCl$_3$) δ 177.0 (2C), 176.9 (2C), 141.0, 139.4, 132.0, 124.4, 124.0, 119.7, 82.4 (t, J$_{CP}$=2.8 Hz, 2C), 82.2 (t, J$_{CP}$=2.8 Hz, 2C), 50.4, 42.4 (t, J$_{CP}$=133.7 Hz), 39.9 (2C), 38.9 (2C), 32.0, 29.0, 28.2 (t, J$_{CP}$=4.1 Hz), 27.0 (12C), 26.5, 25.9, 23.5, 17.8, 15.7 (t, J$_{CP}$=5.8 Hz); $^{31}$P NMR (121 MHz, CDCl$_3$) δ 24.7; HRMS (ES$^+$) m/z calcd for C$_{40}$H$_{69}$N$_3$O$_{14}$P$_2$(M+H)$^+$ 878.4333, found 878.4346.

Example 8: (E)-(((1-(1-(4,8-dimethylnona-3,7-dien-1-yl)-1H-1,2,3-triazol-4-yl)propane-2,2-diyl)bis(oxo-15-phosphanetriyl))tetrakis(oxy))tetrakis(methylene) tetrakis(2,2-dimethylpropanoate) (24)

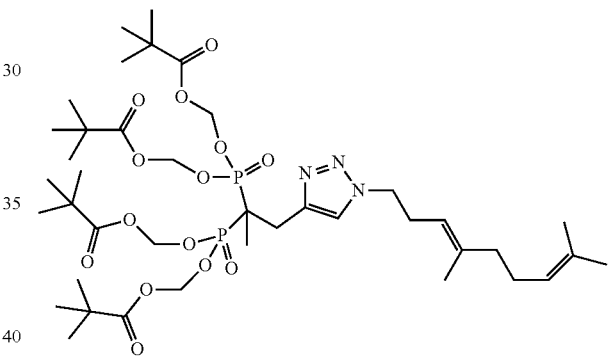

According to the procedure described above for compound 25.

Example 9: tetraethyl (1-(1-(3,7-dimethylocta-2,6-dien-1-yl)-1H-1,2,3-triazol-4-yl)propane-2,2-diyl)bis(phosphonate) (13)

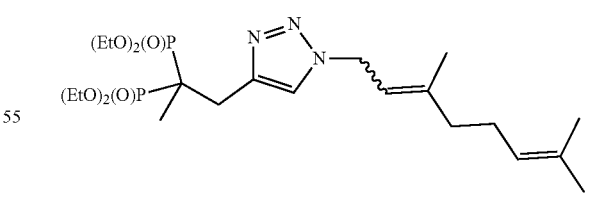

To a stirred solution of bisphosphonate 7 (577 mg, 1.14 mmol) in THF (10 mL) at 0° C. was added NaH (60% in oil, 82 mg, 2.05 mmol) followed by 15-crown-5 (0.04 mL, 0.22 mmol), and the reaction mixture was allowed to stir at 0° C. for 30 min. To the reaction mixture was added MeI (0.12 mL, 1.94 mmol) and the reaction mixture was allowed to stir for 5 h while it warmed to room temperature. The reaction was quenched by addition of NH$_4$Cl and extracted with EtOAc (3×15 mL). After the combined organic layers were dried ($Na_2SO_4$) and filtered, the filtrate was concentrated in vacuo to afford compound 13 (523 mg, 88%) as a yellow oil. Reported is the mixture of E and Z isomers for the 1H NMR data and the major isomer from the $^{13}C$ NMR spectrum: $^1H$ NMR (300 MHz, $CDCl_3$) δ 7.20 (s, 1H), 5.12-5.04 (m, 1H), 4.80-4.67 (m, 1H), 4.58 (t, J=7.1 Hz, 2H), 3.86-3.77 (m, 8H), 2.97 (dd, $J_{HP}$=15.3 Hz, $J_{HP}$=15.3 Hz, 2H), 1.87-1.72 (m, 4H), 1.45 (s, 3H), 1.34-1.32 (m, 3H), 1.27-1.24 (m, 3H), 1.22-1.10 (m, 3H), 0.99-0.91 (m, 12H); $^{13}C$ NMR (75 MHz, $CDCl_3$) δ 142.4 (t, $J_{CP}$=9.7 Hz), 142.3, 131.7, 123.3, 123.2, 117.3, 62.6 (t, $J_{CP}$=3.2 Hz, 2C), 62.3 (t, $J_{CP}$=3.2 Hz, 2C), 47.5, 41.6 (t, $J_{CP}$=132.7 Hz), 39.3, 29.4, 28.7 (t, $J_{CP}$=3.9 Hz), 26.0, 25.5, 17.5, 16.3-16.1 (m, 5C), 16.0; $^{31}P$ NMR (121 MHz, $CDCl_3$) 25.6 ppm; HRMS ($ES^+$) m/z calcd for $C_{23}H_{44}N_3O_6P_2(M+H)^+$ 520.2705, found 520.2695.

Example 10: tetraethyl (1-(1-(4,8-dimethylnona-3,7-dien-1-yl)-1H-1,2,3-triazol-4-yl)propane-2,2-diyl)bis(phosphonate) (10)

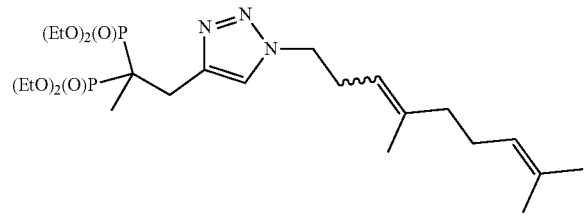

According to the procedure described above for compound 13, a solution of compound 4 (522 mg, 1.01 mmol) in THF (8.5 mL) at 0° C. was treated with NaH (60% in oil, 72 mg, 1.81 mmol), 15-crown-5 (0.04 mL, 0.19 mmol), and MeI (0.11 mL, 2.24 mmol). A parallel workup afforded the bisphosphonate 10 (435 mg, 81%) as a yellow oil. Reported is the mixture of E and Z isomers for the $^1H$ NMR spectrum and the major isomer in the $^{13}C$ NMR spectrum: $^1H$ NMR (300 MHz, $CDCl_3$) δ 7.56 (s, 1H), 5.13-5.02 (m, 2H), 4.31-4.25 (m, 2H), 4.20-4.11 (m, 8H), 3.38-3.27 (m, 2H), 2.57 (dt, J=7.1 Hz, J=7.4 Hz, 2H), 2.07-1.97 (m, 4H), 1.68-1.55 (m, 9H), 1.48 (t, $J_{HP}$=16.7 Hz, 3H), 1.33-1.26 (m, 12H); $^{13}C$ NMR (75 MHz, $CDCl_3$) δ 145.2 (t, $J_{CP}$=9.6 Hz), 139.2, 131.5, 124.0, 123.8, 118.6, 62.8 (t, $J_{CP}$=3.4 Hz, 2C), 62.5 (t, $J_{CP}$=3.4 Hz, 2C), 49.9, 41.5 (t, $J_{CP}$=134.7 Hz), 39.5, 29.6, 29.1, 28.7 (t, $J_{CP}$=4.3 Hz), 26.4, 25.6, 17.6, 16.3 (m, 4H), 16.0; 31P (121 MHz, $CDCl_3$) 26.0 ppm; HRMS ($ES^+$) m/z calcd for $C_{24}H_{46}N_3O_6P_2$ $(M+H)^+$ 534.2862, found 534.2870.

Example 11: tetraethyl (1-(1-(4,8-dimethylnona-3,7-dien-1-yl)-1H-1,2,3-triazol-4-yl)propane-2,2-diyl)(Z)-bis(phosphonate) (11)

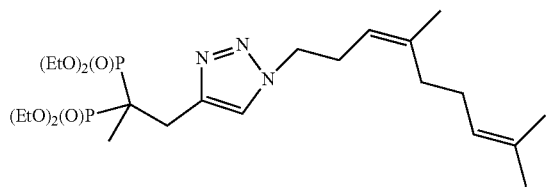

According to the procedure described above for compound 13, a stirred solution of bisphosphonate 5 (691 mg, 1.32 mmol) in THF (11 mL) at 0° C. was treated with NaH (60% in oil, 95 mg, 2.37 mmol), 15-crown-5 (0.05 mL, 0.25 mmol), and MeI (0.14 mL, 2.24 mmol). A parallel workup gave bisphosphonate 11 (685 mg, 96%) as a yellow oil: $^1H$ NMR (300 MHz, $CDCl_3$) δ 7.55 (s, 1H), 5.12-5.03 (m, 2H), 4.26 (t, J=7.4 Hz, 2H), 4.19-4.11 (m, 8H), 3.38-3.26 (m, 2H), 2.56 (dt, J=7.3 Hz, J=7.3 Hz, 2H), 2.04-1.92 (m, 4H), 1.69 (d, J=1.1 Hz, 3H), 1.67 (d, J=0.7 Hz, 3H), 1.59 (d, J=0.7 Hz, 3H), 1.48 (t, $J_{HP}$=16.7 Hz, 3H), 1.32-1.26 (m, 12H); $^{13}C$ NMR (75 MHz, $CDCl_3$) δ 142.1 (t, $J_{CP}$=9.6 Hz), 138.8, 131.5, 123.8, 123.6, 119.4, 62.6 (t, $J_{CP}$=3.4 Hz, 2C), 62.3 (t, $J_{CP}$=3.3 Hz, 2C), 49.9, 41.4 (t, $J_{CP}$=132.8 Hz), 31.6, 28.8, 28.6 (t, $J_{CP}$=4.3 Hz), 26.1, 25.4, 23.1, 17.4, 16.2 (m, 5C); $^{31}P$ (121 MHz, $CDCl_3$) 26.0 ppm; HRMS ($ES^+$) m/z calcd for $C_{24}H_{46}N_3O_6P_2$ $(M+H)^+$ 534.2862, found 534.2859.

Example 12: tetraethyl (1-(1-(4,8-dimethylnona-3,7-dien-1-yl)-1H-1,2,3-triazol-4-yl)propane-2,2-diyl)(E)-bis(phosphonate) (12)

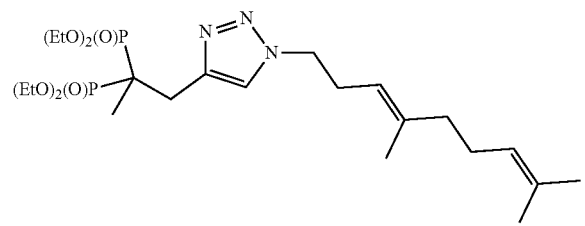

According to the procedure described above for compound 13, a stirred solution of compound 6 (400 mg, 0.77 mmol) in THF (6.5 mL) at 0° C. was treated with NaH (60% in oil, 55 mg, 1.39 mmol), 15-crown-5 (0.03 mL, 0.15 mmol), and MeI (0.08 mL, 1.31 mmol). A parallel workup afforded bisphosphonate 12 (394 mg, 96%) as a yellow oil: $^1H$ NMR (300 MHz, $CDCl_3$) δ 7.37 (s, 1H), 4.95-4.79 (m, 2H), 4.26 (m, 2H), 4.03-3.87 (m, 8H), 3.12 (t, $J_{HP}$=13.9 Hz, 2H), 2.45-2.28 (m, 2H), 1.89-1.67 (m, 4H), 1.46 (s, 3H), 1.38 (s, 3H), 1.34 (m, 3H), 1.27 (t, $J_{HP}$=16.6 Hz, 3H), 1.12-1.03 (m, 12H); 13C NMR (75 MHz, $CDCl_3$) δ 142.4-141.9 (m), 139.0, 131.2, 123.9, 123.7, 118.6, 62.6 (m, 2C), 62.3 (m, 2C), 49.8, 41.5 (t, $J_{CP}$=132.2 Hz), 39.5, 29.5, 29.0, 28.6, 26.4, 25.5, 17.5, 16.2 (4C). 15.8; $^{31}P$ (121 MHz, $CDCl_3$) 25.8 ppm; HRMS ($ES^+$) m/z calcd for $C_{24}H_{46}N_3O_6P_2$ $(M+H)^+$ 534.2862, found 534.2864.

Example 13: tetraethyl (1-(1-(3,7-dimethylocta-2,6-dien-1-yl)-1H-1,2,3-triazol-4-yl)propane-2,2-diyl)(Z)-bis(phosphonate) (14)

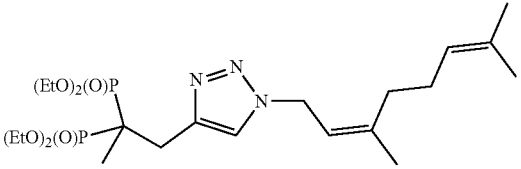

According to the procedure described above for compound 13, a solution of compound 8 (590 mg, 1.17 mmol)

in THF (12 mL) at 0° C. was treated with NaH (60% in oil, 84 mg, 2.11 mmol), 15-crown-5 (0.04 mL, 0.22 mmol), and MeI (0.12 mL, 1.99 mmol). A parallel workup and final purification by column chromatography (10/90 ethanol/hexanes) afforded bisphosphonate 14 (402 mg, 66%) as a yellow oil: $^1$H NMR (300 MHz, CDCl$_3$) δ 7.50 (s, 1H), 5.44-5.36 (m, 1H), 5.13-5.05 (m, 1H), 4.90 (d, J=7.9 Hz, 2H), 4.20-4.08 (t, J=7.1 Hz, 8H), 3.31 (dd, J$_{HP}$=15.5 Hz, J$_{HP}$=15.5 Hz, 2H), 2.22-2.08 (m, 4H), 1.77 (d, J=1.1 Hz, 3H), 1.68 (s, 3H), 1.60 (s, 3H), 1.48 (t, J$_{HP}$=16.7 Hz, 3H), 1.27 (td, J=7.1 Hz, J$_{HP}$=3.0 Hz, 12H); $^{13}$C NMR (75 MHz, CDCl$_3$) δ 142.5 (t, J$_{CP}$=9.9 Hz), 142.4, 132.4, 123.4, 123.1, 118.2, 62.8 (t, J$_{CP}$=3.3 Hz, 2C), 62.5 (t, J$_{CP}$=3.3 Hz, 2C), 47.5, 41.7 (t, J$_{CP}$=133.9 Hz), 32.0, 28.7 (t, J$_{CP}$=4.4 Hz), 26.3, 25.6, 23.3, 17.6, 16.3-16.1 (m, 5C); $^{31}$P NMR (121 MHz, CDCl$_3$) 26.0 ppm; HRMS (ES$^+$) m/z calcd for C$_{23}$H$_{44}$N$_3$O$_6$P$_2$ (M+H)$^+$ 520.2705, found 520.2710.

Example 14: tetraethyl (1-(1-(3,7-dimethylocta-2,6-dien-1-yl)-1H-1,2,3-triazol-4-yl)propane-2,2-diyl) (E)-bis(phosphonate) (15)

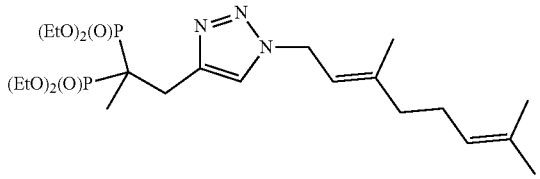

According to the procedure described above for compound 13, a solution of bisphosphonate 9 (300 mg, 0.59 mmol) in THF (6 mL) at 0° C. was treated with NaH (60% in oil, 42 mg, 1.06 mmol), 15-crown-5 (0.02 mL, 0.11 mmol), and MeI (0.06 mL, 1.00 mmol). A parallel workup and final purification by column chromatography (10/90 ethanol/hexanes) provided bisphosphonate 15 (125 mg, 41%) as a yellow oil: $^1$H NMR (300 MHz, CDCl$_3$) δ 7.51 (s, 1H), 5.44-5.36 (m, 1H), 5.08-5.01 (m, 1H), 4.92 (d, J=7.3 Hz, 2H), 4.19-4.09 (m, 8H), 3.31 (dd, J$_{HP}$=15.5 Hz, J$_{HP}$=15.5 Hz, 2H), 2.12-2.02 (m, 4H), 1.77 (d, J$_{HP}$=1.1 Hz, 3H), 1.67 (d, J=1.1 Hz, 3H), 1.58 (s, 3H), 1.49 (t, J=16.7 Hz, 3H), 1.28 (td, J=7.1 Hz, J$_{HP}$=3.1 Hz, 12H); $^{13}$C NMR (75 MHz, CDCl$_3$) δ 142.7 (t, J$_{CP}$=10.0 Hz), 142.7, 132.2, 123.5, 123.5, 117.4, 63.0 (t, J$_{CP}$=3.3 Hz, 2C), 62.6 (t, J$_{CP}$=3.3 Hz, 2C), 47.8, 41.9 (t, J$_{CP}$=133.9 Hz), 39.5, 28.7 (t, J$_{CP}$=4.3 Hz), 26.3, 25.7, 17.7, 16.6-16.3 (m, 6C); $^{31}$P NMR (121 MHz, CDCl$_3$) 26.0 ppm; HRMS (ES$^+$) m/z calcd for C$_{23}$H$_{44}$N$_3$O$_6$P$_2$ (M+H)$^+$ 520.2705, found 520.2706.

Biological Assays

Figure 3:
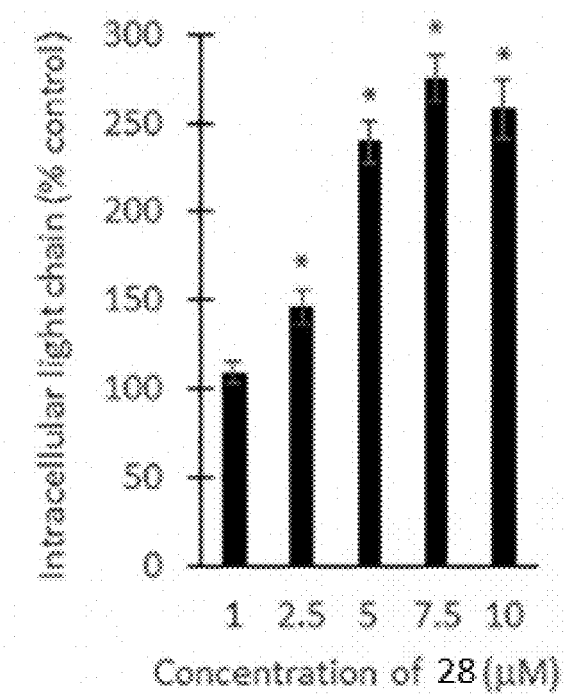
FIG. 3 shows the cellular activity of compound 28. RPMI-8226 cells were incubated for 48 h in the presence or absence of lovastatin (Lov, 10 µM) or varying concentrations of the test compound. Intracellular lambda light chain concentrations were determined via ELISA. Data are expressed as a percentage of control (mean±SD, n=3). The * denotes p<0.05 per unpaired two-tailed t-test.
Figure 4:
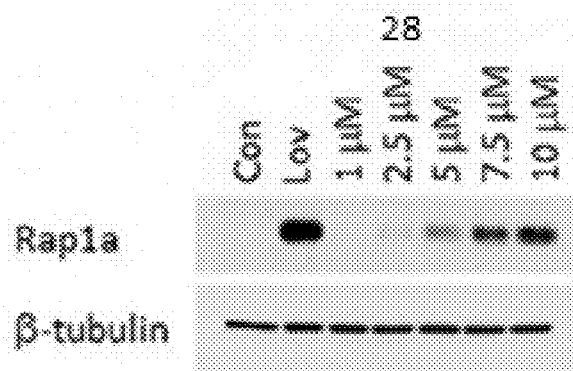
FIG. 4 shows the effects of 28 on protein geranylgeranylation using immunoblot analysis of Rap1a (antibody detects only unmodified protein) and R-tubulin (as a loading control).
Figure 5:
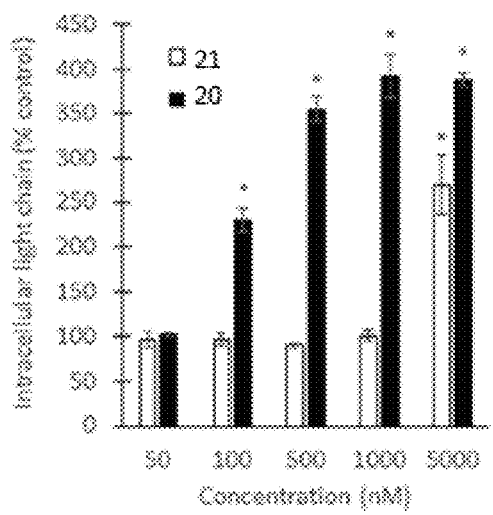
FIG. 5 shows the effects of olefin stereochemistry on activity of the α-methylated triazole bisphosphonates. RPMI-8226 cells were incubated for 48 h in the presence or absence of lovastatin (Lov, 10 µM) or varying concentrations of the test compounds. Intracellular lambda light chain concentrations were determined via ELISA. Data are expressed as a percentage of control (mean±SD, n=3). The * denotes p<0.05 per unpaired two-tailed t-test.
Figure 5:
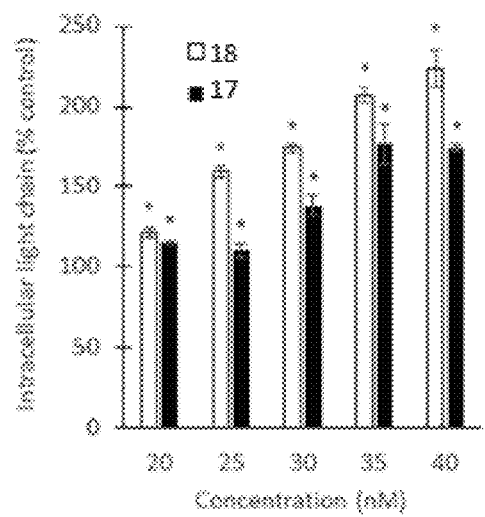
Figure 6:
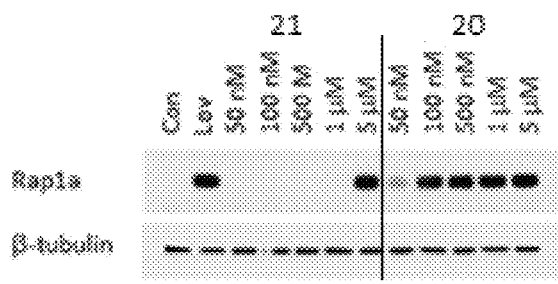
FIG. 6 shows the effects of olefin stereochemistry on activity of the α-methylated triazole bisphosphonates using immunoblot analysis of Rap1a (antibody detects only unmodified protein) and R-tubulin (as a loading control).
Figure 6:
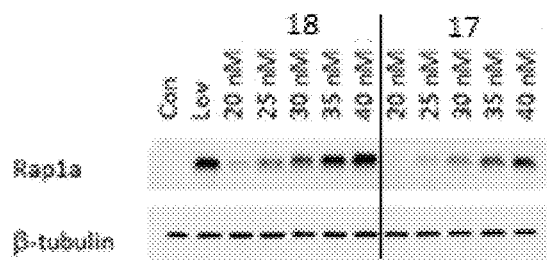

The impact of substituents at the α-carbon of the compounds disclosed herein on cellular activity was assessed in myeloma cells. Impairment of cellular protein geranylgeranylation was determined via two methods: 1) ELISA for intracellular lambda light chain which is a marker for disruption of Rab GTPase geranyl-geranylation (FIGS. 1, 3, 5, 7) and 2) immunoblot analysis for unmodified Rap1a (a substrate of GGTase I) (FIGS. 2, 4, 6, 8). Lovastatin, an HMG-CoA reductase inhibitor, was included as a positive control. In both the C$_{10}$alkylene and C$_{11}$alkylene compounds, the addition of a methyl group at the α-carbon resulted in enhanced cellular activity. The higher homologue which bears an ethyl group (28) at the α-carbon was found to be less potent than either the parent compound 31 (see comparative examples) or the methyl analogue 19 (FIGS. 3 and 4), and so higher homologues were not pursued further. Next, the impact of the olefin stereochemistry on biological activity was determined. As shown in FIG. 5, the Z-configuration of the C$_{10}$alkenyl compound 20 was approximately 50-fold more potent than the E-isomer 21. Interestingly, however, the activity of the two C$_{11}$alkenyl compounds (18 and 17) was very similar, with the E-isomer (18) slightly more potent than the Z-isomer (17).

Figure 9:
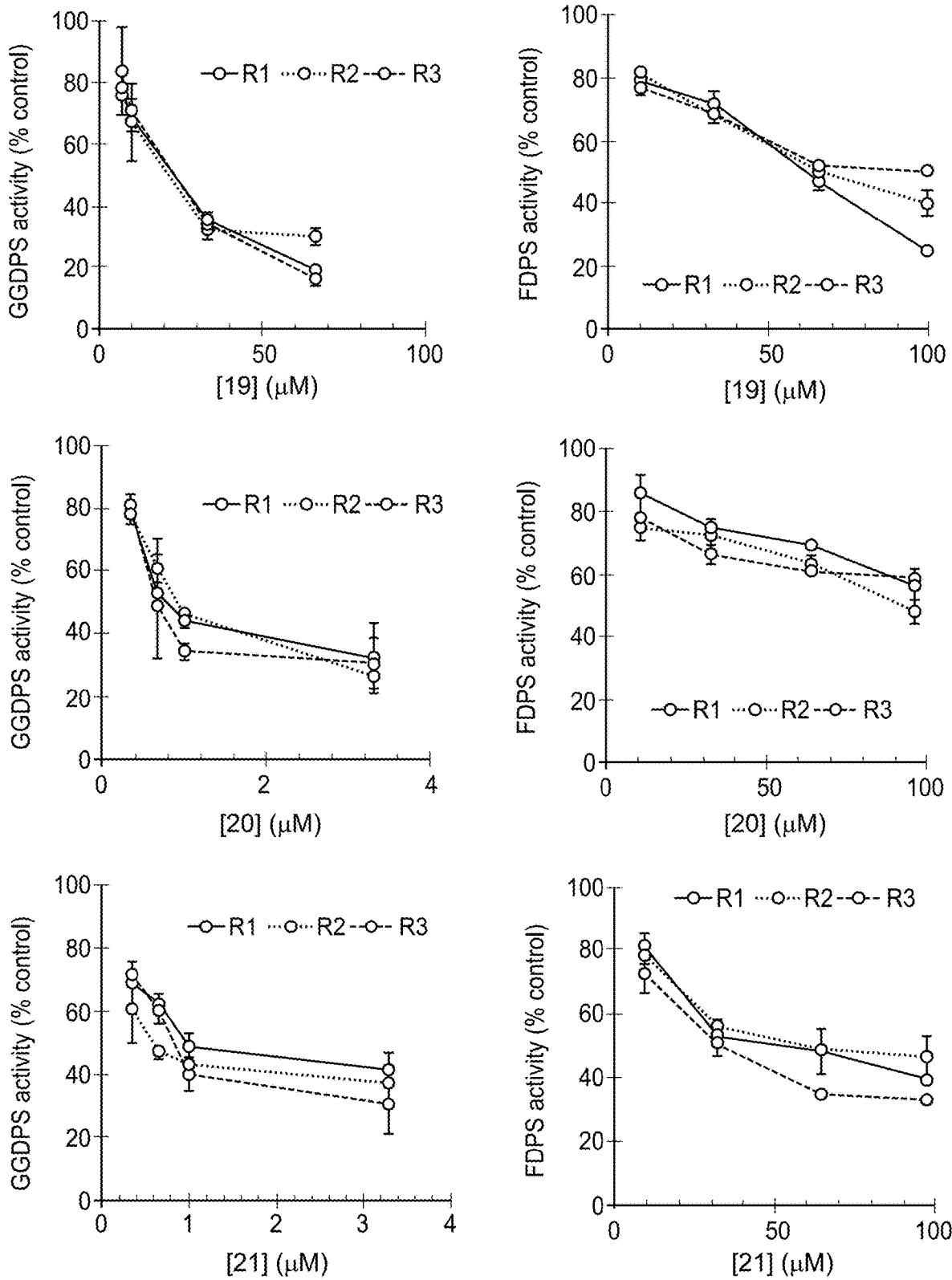
FIG. 9 GGDPS and FDPS enzyme assay data for compounds 19, 20, and 21. Each assay was performed in three independent experiments (R1, R2, R3) and each compound was tested in duplicate at each concentration. Data are displayed as percent control (mean±SD).
Figure 10:
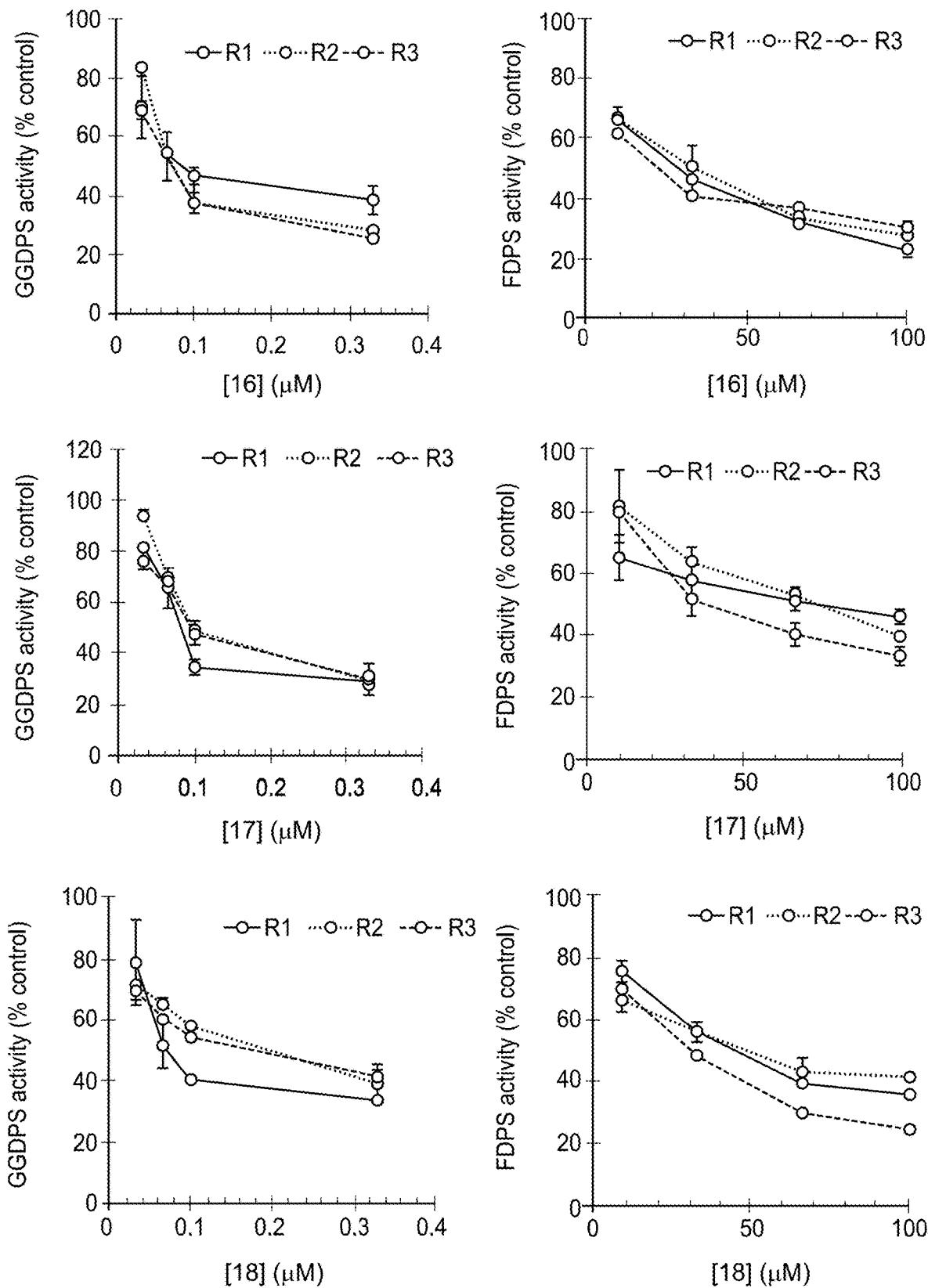
FIG. 10 shows GGDPS and FDPS enzyme assay data for compounds 16, 17, and 18. Each assay was performed in three independent experiments (R1, R2, R3) and each compound was tested in duplicate at each concentration. Data are displayed as percent control (mean±SD).
Figure 11:
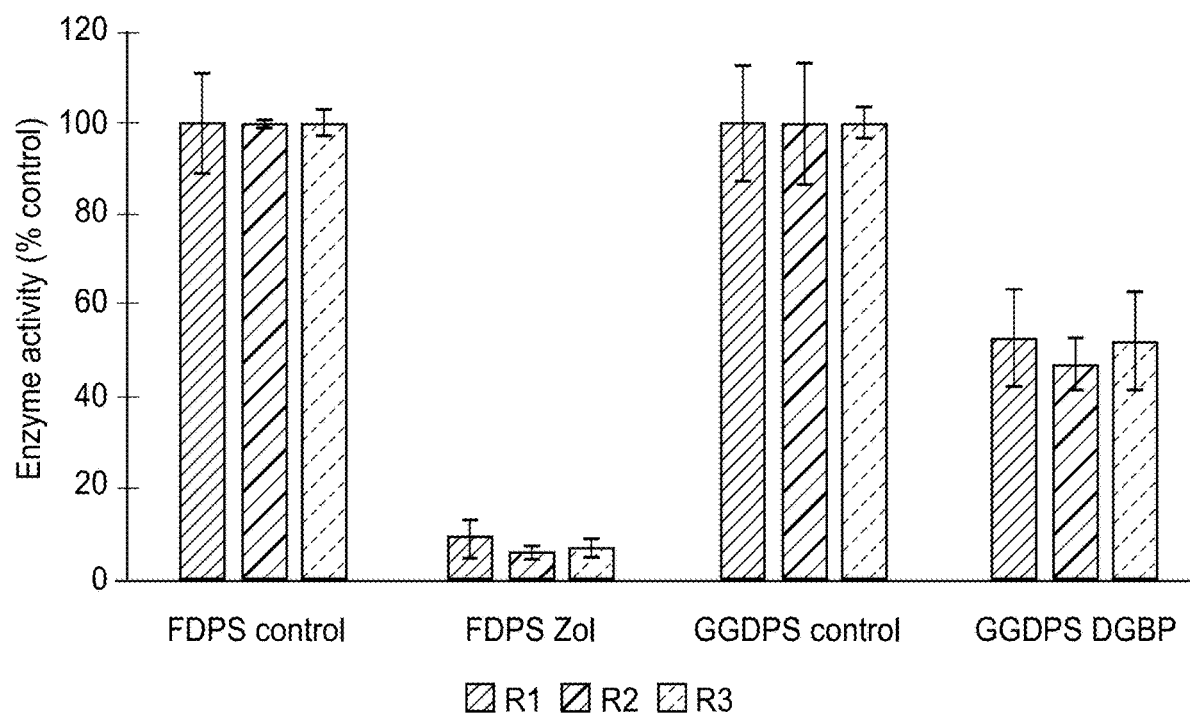
FIG. 11 shows positive controls used for the GGDPS and FDPS enzyme assays. Results from three representative assays are shown (R1, R2, R3) with each condition tested in duplicate (data are displayed as percent control (mean±SD). Abbreviations: Zol, zoledronic acid (50 nM); DGBP, digeranyl bisphosphonate (0.2 µM).

Consistent with the cellular assays, the enzymatic assays (FIG. 9-11) revealed that the methylated mixture 19 is more potent than its corresponding non-methylated analogue 31, and that the Z isomer 20 is more potent than the E isomer 21 (Table 1). In contrast, the GGDPS inhibitory activity of the α-methylated mixture 16 was very similar to the individual isomers (17 and 18). There was specificity for GGDPS over FOPS, with at least 3.5-fold selectivity in the case of the least potent GGDPS inhibitor (21) and 240- to 690-fold selectivity for the methylated mixture series 16 and 19.

Figure 7:
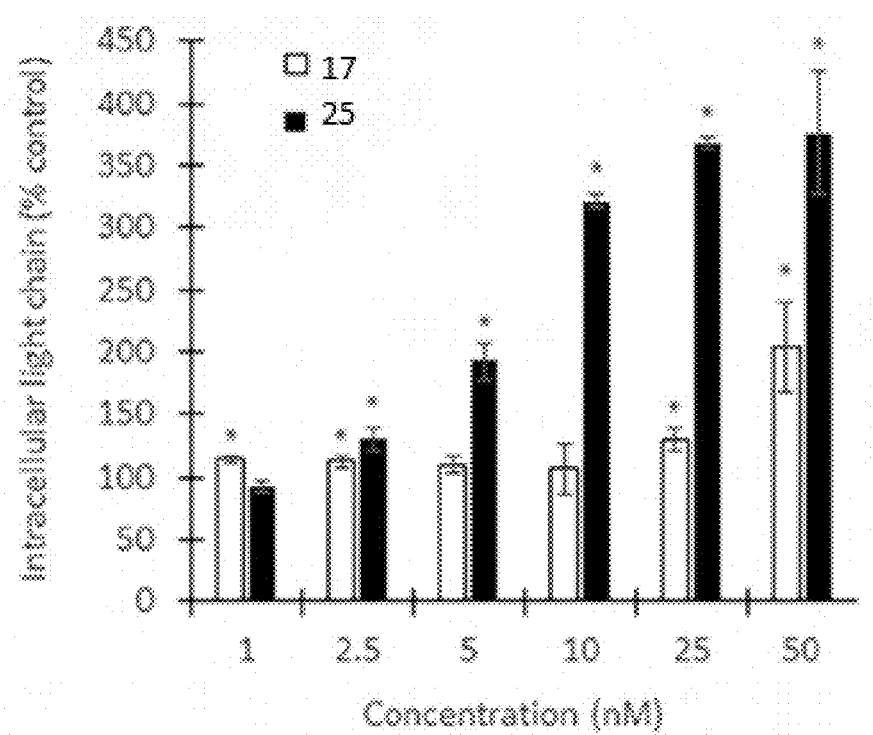
FIG. 7 shows compound 25 enhances cellular activity compared to compound 17. RPMI-8226 cells were incubated for 48 h in the presence or absence of lovastatin (Lov, 10 µM) or varying concentrations of the test compounds. Intracellular lambda light chain concentrations were determined via ELISA. Data are expressed as a percentage of control (mean±SD, n=3). The * denotes p<0.05 per unpaired two-tailed t-test.
Figure 8:
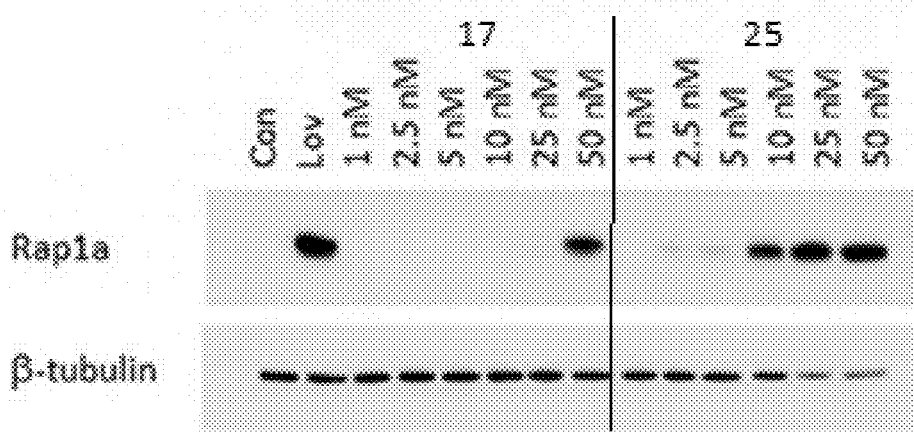
FIG. 8 shows a comparison of the effects of 25 and 17 on protein geranylgeraylation using immunoblot analysis of Rap1a (antibody detects only unmodified protein) and β-tubulin (as a loading control).

Finally, the activity of the POM-prodrug 37 was assessed in comparison to the corresponding salt. As shown in FIG. 7, the POM-version of 17 (25) displayed enhanced cellular potency compared to the corresponding salt with approximately 10-fold improvement in activity.

TABLE 1

| Compound | GGDPS IC$_{50}$ (μM) | FDPS IC$_{50}$ (μM) | Selectivity for GGDPS to FDPS | Cellular LEC[1] (μM) |
|---|---|---|---|---|
| 16 | 1.27 ± 0.303 | 62.2 ± 7.22 | 49 | 0.1 |
| 17 | 0.920 ± 0.089 | >100 | >108 | 0.1 |
| 18 | 20.5 ± 2.30 | 71.4 ± 24.2 | 3.5 | 5.0 |
| 19 | 0.100 ± 0.019 | 24.1 ± 3.15 | 241 | 0.03 |
| 20 | 0.086 ± 0.022 | 59.6 ± 15.0 | 693 | 0.025 |
| 21 | 0.125 ± 0.027 | 43.1 ± 2.98 | 345 | 0.02 |
| 28 | 5.85 ± 1.30 | 94.3 ± 20.6 | 16 | 2.5 |

[1]Cellular LEC (lowest effective concentration) is defined as the lowest concentration for which an unmodified Rap1a band is visible in the immunoblot and a statistically significant increase in intracellular lambda light chain is observed in the ELISA.

Immunoblot analysis (FIG. 2, 4, 6, 8): Multiple myeloma cells were incubated (37° C. and 5% CO$_2$) with test compounds for 48 hours in RPMI-1640 media containing 10% fetal bovine serum and penicillin-streptomycin. Whole cell lysate was obtained using RIPA buffer (0.15 M NaCl, 1% sodium deoxycholate, 0.1% SODS, 1% Triton (v/v) X-100, 0.05 M Tris HCl) containing protease and phosphatase inhibitors. Protein content was determined using the bicinchoninic acid (BCA) method (Pierce Chemical, Rockford, IL). Equivalent amounts of cell lysate were resolved by SODS-PAGE, transferred to polyvinylidene difluoride membrane, probed with the appropriate primary antibodies, and detected using HRP-linked secondary antibodies and Bio-Rad Clarity ECL Substrate Western blotting reagents per manufacturer's protocols.

Lambda light chain ELISA (FIG. 1, 3, 5, 7): Human lambda light chain kit (Bethyl Laboratories, Montgomery, TX) was used to quantify intracellular monoclonal protein levels of whole cell lysate. Lambda light chain levels were normalized to total protein levels (as determined by BCA).

GGDPS Enzyme assay (FIG. 9, 10, 11): Recombinant GGDPS was obtained from MyBioSource (San Diego, CA). Recombinant enzyme (20 nM GGDPS) was incubated with assay buffer (50 mM Tris-HCl, pH 7.7, 20 mM MgCl$_2$, 5 mM TCEP, 5 μg/mL BSA) and test compounds for 10 minutes at room temperature. The reaction was initiated by the addition of 10 μM FPP and 10 μM [$^{14}$C]-IPP and carried out at 37° C. for 30 minutes. The reaction was stopped by the addition of saturated NaCl. Radiolabeled GGPP was extracted with n-butanol and counted via liquid scintillation counting. CompuSyn software (ComboSyn, Inc.) was used to analyze the concentration response curves and determine the $IC_{50}$ values.

Comparative Examples

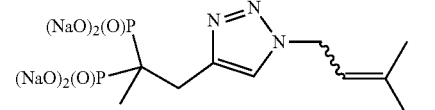

29 E isomer GGDPS $IC_{50}$ = 17 μM
30 Z isomer GGDPS $IC_{50}$ = 0.38 μM
31 2:1 E:Z isomer GGDPS $IC_{50}$ = 2.2 μM

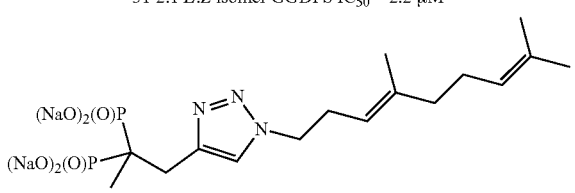

32 E isomer GGDPS $IC_{50}$ = 0.17 μM
33 Z isomer GGDPS $IC_{50}$ = 0.075 μM
34 3:1 E:Z isomer GGDPS $IC_{50}$ = 0.045 μM

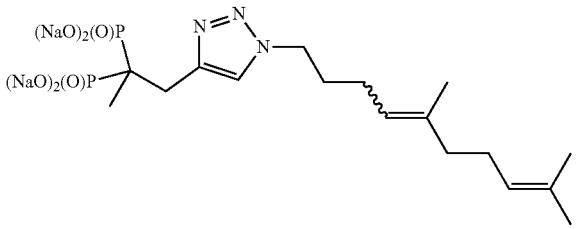

35 E isomer GGDPS IC50 = 2.56 μM
36 Z isomer GGDPS $IC_{50}$ = 1.29 μM

What is claimed:

1. A pharmaceutical composition comprising a compound of Formula (I), or a pharmaceutically acceptable salt thereof, and a pharmaceutically acceptable excipient, wherein Formula (I) is:

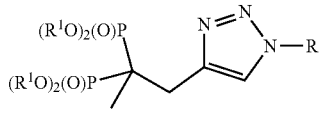

(I)

wherein:
each $R^1$ comprises a protecting group, H, or M;
R comprises $C_{10-15}$alkyl, $C_{10-15}$alkenyl, $C_{10-15}$hydroxyalkyl or $C_{10-15}$hydroxyalkenyl; and
M is a metal ion selected from Li, Na, and K.

2. The pharmaceutical composition of claim 1, wherein R is $C_{10-15}$alkenyl and the $C_{10-15}$alkenyl comprises 1, 2, or 3 double bonds.

3. The pharmaceutical composition of claim 1, wherein R comprises $C_{11}$alkenyl.

4. The pharmaceutical composition of claim 1, wherein R is $C_{10-15}$hydroxyalkenyl and the $C_{10-15}$hydoxyalkenyl comprises 1, 2, or 3 double bonds.

5. The pharmaceutical composition of claim 1, wherein R is selected from the group consisting of:

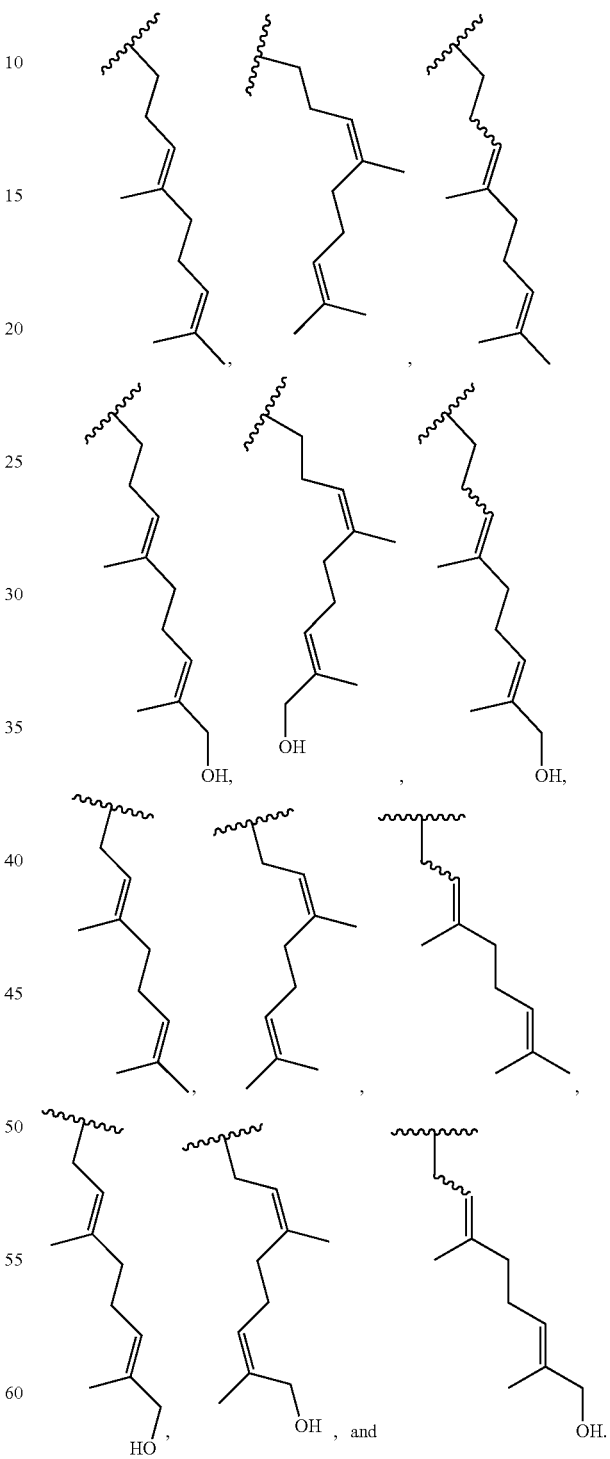

6. The pharmaceutical composition of claim 1, wherein the compound of Formula (I) is selected from the group consisting of:

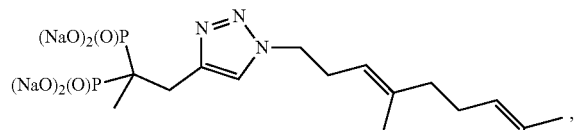
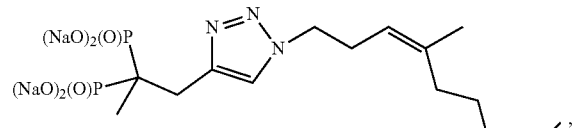
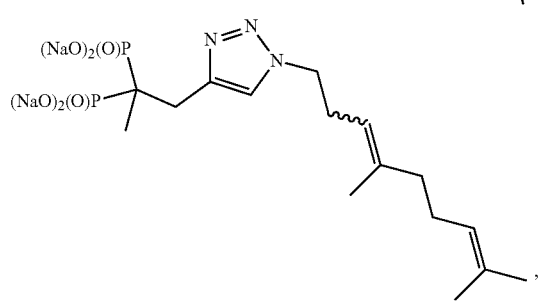
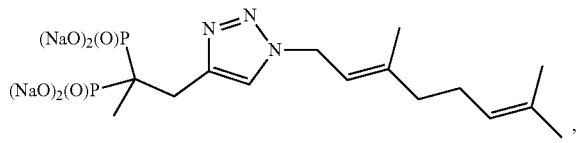
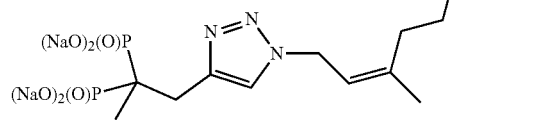
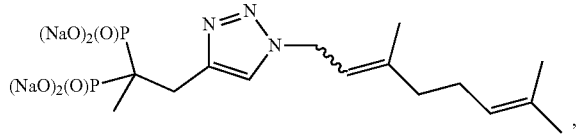
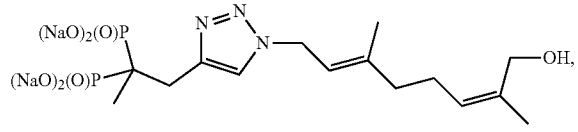
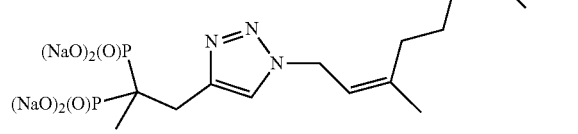
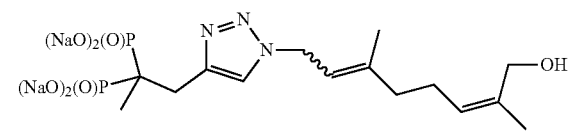
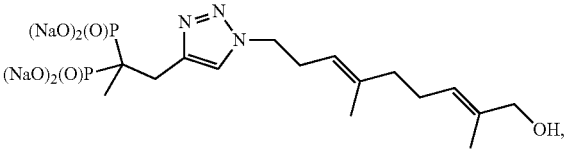
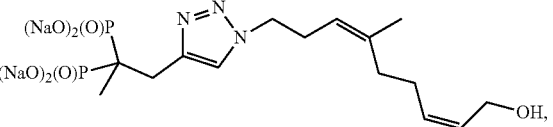
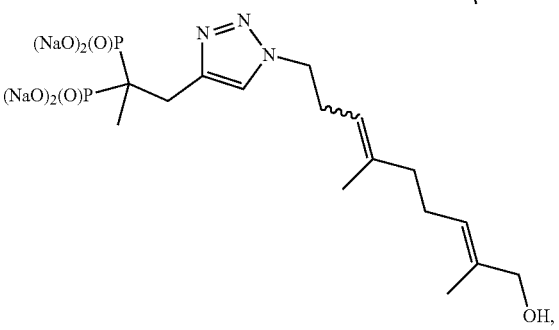
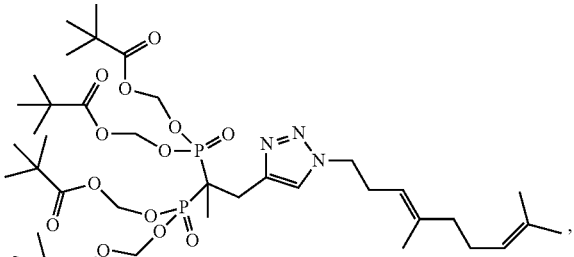
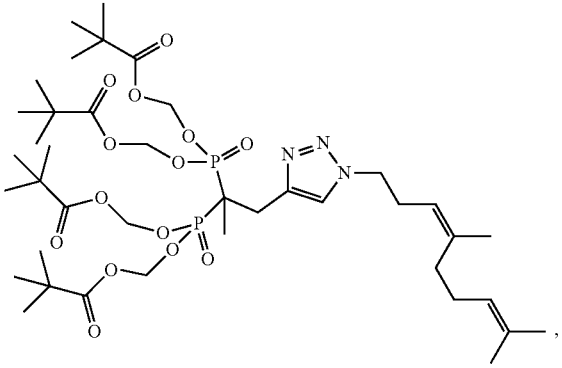
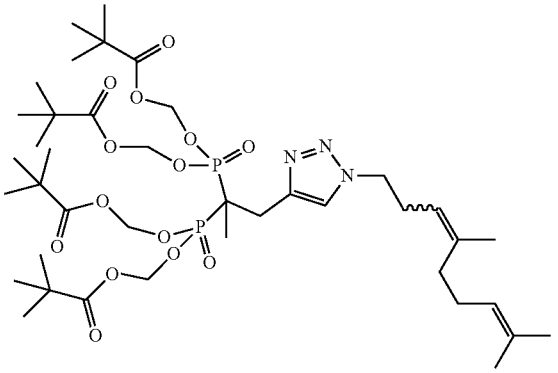

-continued

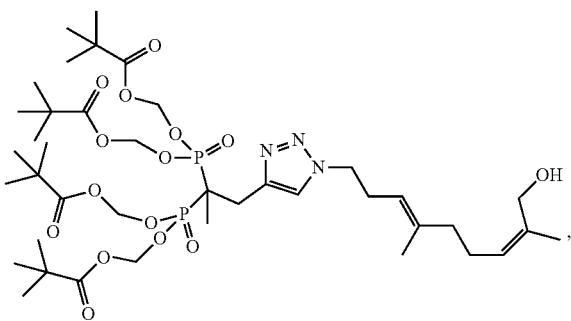

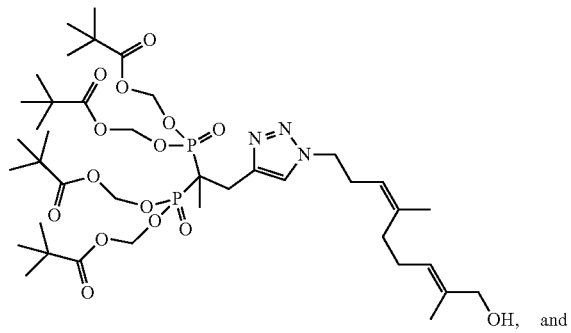

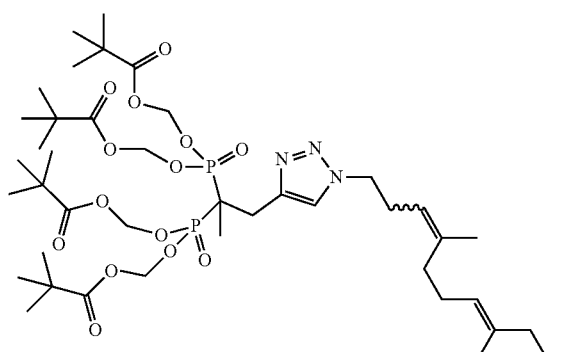

or a pharmaceutically acceptable salt thereof.

7. The pharmaceutical composition of claim 1, wherein the compound of Formula (I) has a structure of:

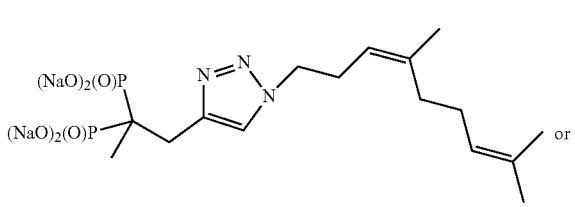

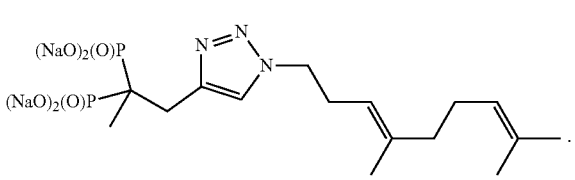

8. The pharmaceutical composition of claim 1, wherein the compound of Formula (I) has a structure of:

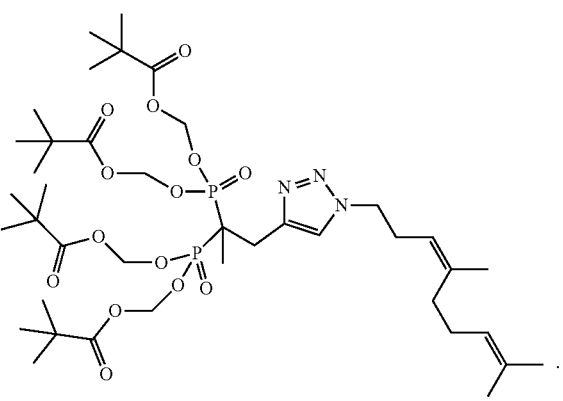 [SMILES: CC(C)=CCC/C(C)=C\CCn1cc(CC(C)(P(=O)(OCOC(=O)C(C)(C)C)OCOC(=O)C(C)(C)C)P(=O)(OCOC(=O)C(C)(C)C)OCOC(=O)C(C)(C)C)nn1]

and the wavy line indicates a mixture of E and Z isomers.

9. The pharmaceutical composition of claim 1, wherein the compound of Formula (I) has a structure of:

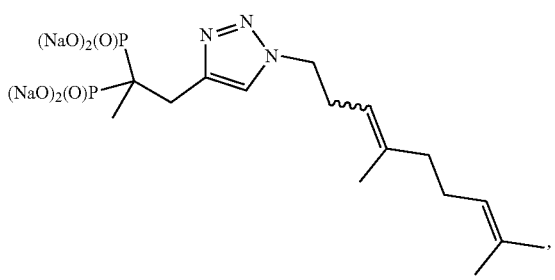

10. The pharmaceutical composition of claim 1, wherein the compound of Formula (I) has a structure of:

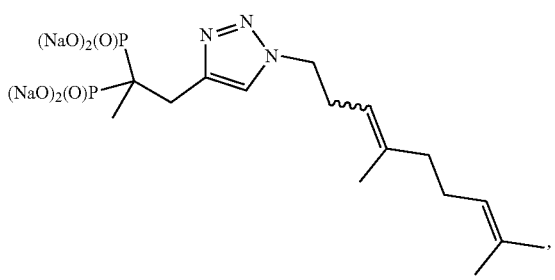

and the wavy line indicates a mixture of E and Z isomers.

11. The pharmaceutical composition of claim 10, wherein the isomers have a ratio of about 2.6:1 E:Z.

12. The pharmaceutical composition of claim 1 is an oral pharmaceutical composition.

13. The pharmaceutical composition of claim 1, wherein the pharmaceutically acceptable excipient comprises one or more of the group of: adjuvants, fillers, binders, humectants, disintegrating agents, solution retarders, absorption accelerators, adsorbents, lubricants, and buffering agents.

14. A method for treating cancer in a subject suffering from the cancer, comprising administering to the subject the pharmaceutical composition of claim 1, wherein the cancer is selected from the group consisting of leukemia, lymphoma, bone cancer, prostate cancer, breast cancer, sarcoma, lung cancer, bladder cancer, multiple myeloma, skin cancer, brain cancer, thyroid cancer, stomach cancer, ovarian cancer, liver cancer, and colon cancer.

15. The method of claim 14, wherein the cancer is multiple myeloma.

16. The method of claim 14, further comprising administering to the subject a second therapeutic.

17. The method of claim 16, wherein the second therapeutic is aspirin, sulindac, curcumin, alkylating agents, nitrogen mustard, mechlor-ethamine, cyclophosphamide, ifosfamide, melphalan, chlorambucil, nitrosourea, carmustine (BCNU), lomustine (CCNU), semustine (methyl-CCNU); ethylenimine, methylmelamine, thriethylenemelamine (TEM), triethylene, thiophosphoramide (thiotepa), hexamethylmelamine (HMM, altretamine); alkyl sulfonate, busulfan; triazine, dacarbazine (DTIC); a folic acid analog, methotrexate, trimetrexate, pyrimidine analog, 5-fluorouracil, fluorodeoxyuridine, gemcitabine, cytosine arabinoside (AraC, cytarabine), 5-azacytidine, 2,2'-difluorodeoxycytidine, purine analog, 6-mercaptopurine, 6-thioguanine, azathioprine, 2'-deoxycoformycin (pentostatin), erythrohydroxynonyladenine (EHNA), fludarabine phosphate, 2-chlorodeoxyadenosine (cladribine, 2-CdA); antimitotic drug, paclitaxel, *vinca* alkaloid, vinblastine (VLB), vincristine, vinorelbine, taxotere, estramustine, estramustine phosphate; epipodophylotoxin, etoposide, teniposide; antibiotic, actimomycin D, daunomycin (rubidomycin), doxorubicin, mitoxantrone, idarubicin, bleomycins, plicamycin (mithramycin), mitomycinC, actinomycin; L-asparaginase; interferon-alpha, IL-2, G-CSF, GM-CSF; platinum coordination complex, cisplatin, carboplatin, anthracenedione, mitoxantrone, hydroxyurea, methylhydrazine derivative, N-methylhydrazine (MIH), procarbazine, adrenocortical suppressant, mitotane (o,p'-DDD), aminoglutethimide; adrenocorticosteroid antagonist, prednisone, dexamethasone, aminoglutethimide; progestin, hydroxyprogesterone caproate, medroxyprogesterone acetate, megestrol acetate; estrogen, diethylstilbestrol, ethinyl estradiol; antiestrogen, tamoxifen; androgen, testosterone propionate, fluoxymesterone; antiandrogen, flutamide, gonadotropin-releasing hormone analog, leuprolide; non-steroidal antiandrogen, flutamide; kinase inhibitor, histone deacetylase inhibitor, methylation inhibitor, proteasome inhibitor, monoclonal antibody, oxidant, anti-oxidant, telomerase inhibitor, BH3 mimetic, ubiquitin ligase inhibitor, immunomodulatory drug, checkpoint inhibitor, or a stat inhibitor.

18. A method of treating a disease associated with aberrant geranylgeranyl diphosphate synthase ("GGDPS") activity in a subject suffering from the disease, comprising administering to the subject the pharmaceutical composition of claim 1, wherein the disease is selected from amyloidosis, autoimmune disorder, and infectious disease.

19. A method of preparing the compound of Formula (I), or a pharmaceutically acceptable salt thereof, wherein Formula (I) is:

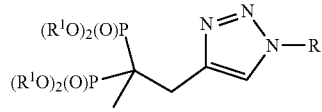

wherein:
each $R^1$ comprises a protecting group, H, or M;
R comprises $C_{10-15}$alkyl, $C_{10-15}$alkenyl, $C_{10-15}$hydroxyalkyl or $C_{10-15}$hydroxyalkenyl; and
M is a metal ion selected from Li, Na, and K,
the method comprising:
admixing sodium hydride and MeI with a compound selected from the group of:

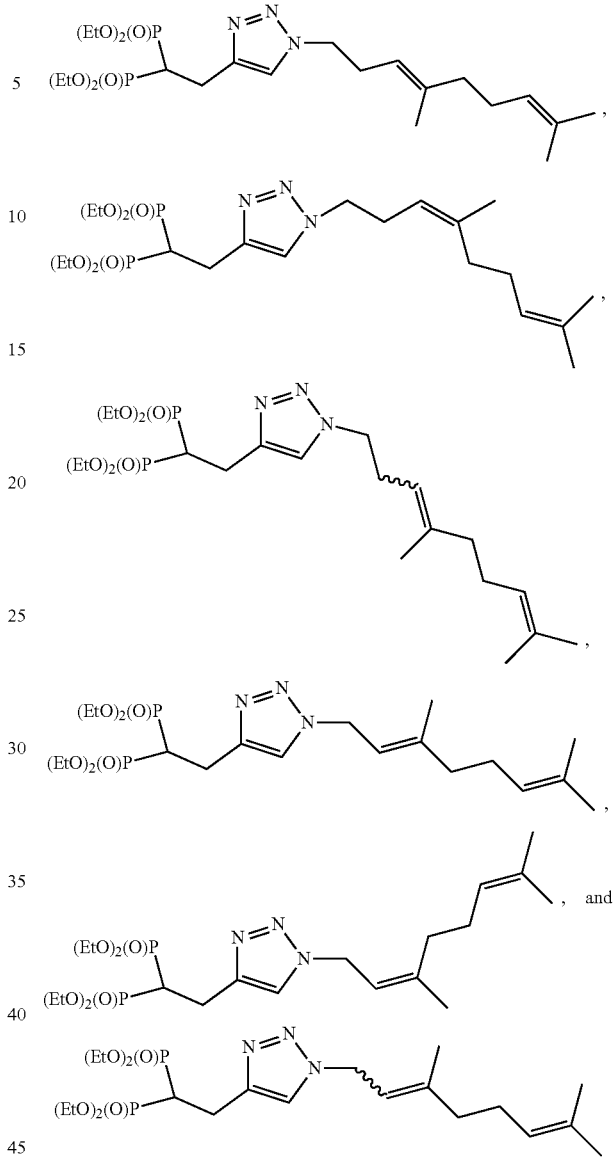

under conditions to methylate the α-carbon of the compounds to form a compound selected from the group of:

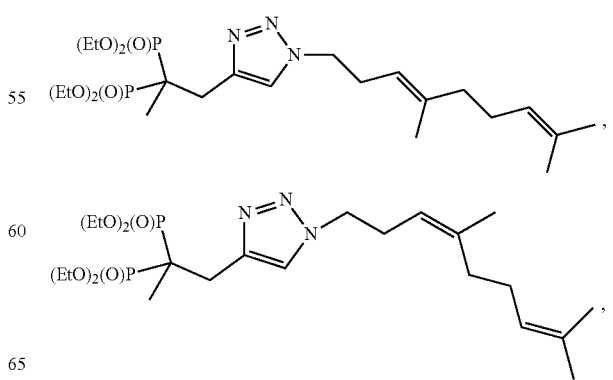

-continued

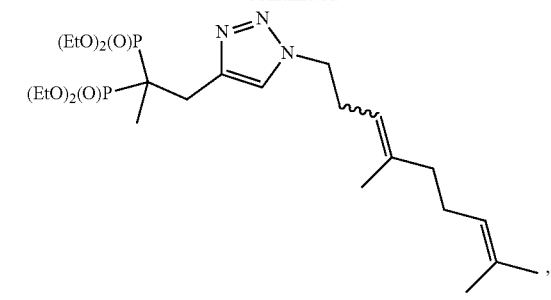

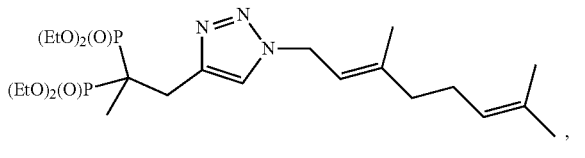
, and

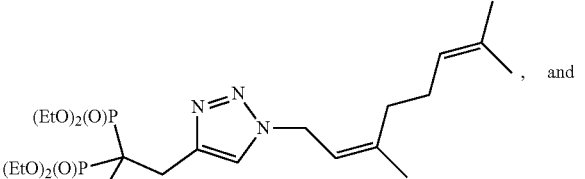
;

and admixing trimethylsilylbromide, collidine, and sodium hydroxide with a compound selected from the group of:

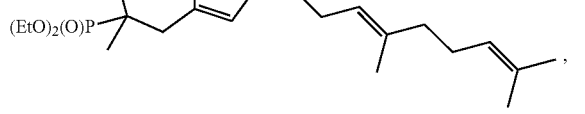
,

-continued

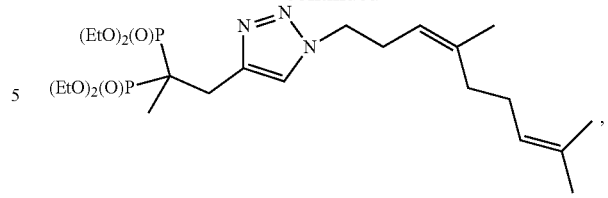
,

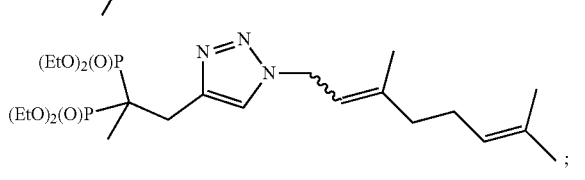
,

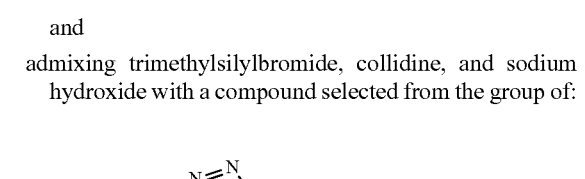
, and under conditions sufficient to form a compound of formula (I).

20. The pharmaceutical composition of claim 1, wherein $R^1$ comprises a protecting group, H, or M; R comprises $C_{10-12}$alkenyl or $C_{10-15}$hydroxyalkenyl; and M is a metal ion selected from Li, Na, and K.

* * * * *